(12) United States Patent
Mochizuki et al.

(10) Patent No.: US 10,045,936 B2
(45) Date of Patent: Aug. 14, 2018

(54) METHOD FOR MANUFACTURING TRANSDERMAL-ABSORPTION SHEET

(71) Applicant: FUJIFILM Corporation, Tokyo (JP)

(72) Inventors: Aya Mochizuki, Ashigarakami-gun (JP); Seiji Kasahara, Ashigarakami-gun (JP); Yanlong Che, Ashigarakami-gun (JP); Shotaro Ogawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 398 days.

(21) Appl. No.: 14/709,644

(22) Filed: May 12, 2015

(65) Prior Publication Data
US 2015/0238413 A1  Aug. 27, 2015

Related U.S. Application Data

(63) Continuation of application No. PCT/JP2013/080536, filed on Nov. 12, 2013.

(30) Foreign Application Priority Data

Nov. 13, 2012 (JP) .................................. 2012-249679

(51) Int. Cl.
A61K 9/00 (2006.01)
A61M 37/00 (2006.01)
(Continued)

(52) U.S. Cl.
CPC ....... A61K 9/0021 (2013.01); A61M 37/0015 (2013.01); B29C 39/24 (2013.01);
(Continued)

(58) Field of Classification Search
CPC ...... A61M 2037/0023; A61M 37/0015; A61M 2037/0046; A61M 2037/0053;
(Continued)

(56) References Cited

U.S. PATENT DOCUMENTS 6,231,333 B1 *  5/2001  Gruber ................ B23K 3/0607
                                              118/256
7,703,658 B2 *  4/2010  Gormley .............. B23K 3/0623
                                              228/180.22
(Continued)

FOREIGN PATENT DOCUMENTS

JP  2007-260351 A  10/2007
JP  2009-195583 A   9/2009
(Continued)

OTHER PUBLICATIONS

English translation of the International Preliminary Report on Patentability, (Forms PCT/IB/338 and PCT/IPEA/409), dated May 14, 2015, for International Application PCT/JP2013/080536.
(Continued)

Primary Examiner — Alison L Hindenlang
Assistant Examiner — Jerzi H Moreno Hernandez
(74) Attorney, Agent, or Firm — Birch, Stewart, Kolasch & Birch, LLP

(57) ABSTRACT

A method is provided which enables a drug to be concentrated at needle-like protruding portions and which further allows transdermal-absorption sheets to be manufactured at high production efficiency. The method repeats a step of feeding a drug-containing solution from a liquid feeding apparatus to a mold and filling needle-like recessed portions with the drug-containing solution through a nozzle aligned over the needle-like recessed portions in a state where the nozzle and a front surface of the mold are brought into contact with each other, and a step of moving the liquid feeding apparatus relative to the mold in a state where the nozzle and the front surface of the mold are brought into contact with each other. Thus, the two-dimensionally arranged needle-like recessed portions are filled with the drug-containing solution.

19 Claims, 17 Drawing Sheets

(51) Int. Cl.
*B29C 39/24* (2006.01)
*B29L 31/00* (2006.01)

(52) U.S. Cl.
CPC ............... *A61M 2037/0046* (2013.01); *A61M 2037/0053* (2013.01); *B29L 2031/756* (2013.01); *B29L 2031/7544* (2013.01); *F04C 2270/0421* (2013.01)

(58) Field of Classification Search
CPC ........... A61K 9/0021; B29L 2031/7544; B29L 2031/756; B29C 39/24; F04C 2270/0421
See application file for complete search history.

(56) References Cited

U.S. PATENT DOCUMENTS

| | | | |
|---|---|---|---|
| 2008/0269685 A1 | 10/2008 | Singh et al. | |
| 2008/0285136 A1* | 11/2008 | Jacobowitz | B29D 11/00365 359/619 |
| 2009/0182306 A1* | 7/2009 | Lee | A61K 9/0021 604/506 |
| 2009/0234301 A1* | 9/2009 | Tomono | A61M 37/0015 604/272 |
| 2010/0084437 A1* | 4/2010 | Biggs | B22D 37/005 222/590 |
| 2011/0042847 A1* | 2/2011 | Ogawa | B29C 33/306 264/219 |
| 2011/0152792 A1* | 6/2011 | Takada | A61M 37/0015 604/272 |
| 2011/0192562 A1 | 8/2011 | Motoi et al. | |
| 2011/0195124 A1* | 8/2011 | Jin | A61K 9/0021 424/486 |
| 2012/0078189 A1 | 3/2012 | Ogawa et al. | |
| 2012/0283695 A1* | 11/2012 | Chen | B82Y 5/00 604/506 |
| 2014/0188041 A1* | 7/2014 | Moore | A61K 9/0021 604/46 |

FOREIGN PATENT DOCUMENTS

| | | | |
|---|---|---|---|
| JP | 2010-1233 A | 1/2010 | |
| JP | 2010-47576 A | 3/2010 | |
| JP | 2011-78617 A | 4/2011 | |
| JP | 2012-196426 A | 10/2012 | |
| JP | 2012-200572 A | 10/2012 | |
| JP | 2012200572 A | * 10/2012 | ........ A61M 37/0015 |

OTHER PUBLICATIONS

Extended European Search Report dated Jun. 15, 2016 for corresponding Application No. 13855660.0.
International Preliminary Report on Patentability (PCT/IPEA/409), issued in PCT/JP2013/080536, dated Feb. 5, 2015.
International Search Report, issued in PCT/JP2013/080536, dated Feb. 25, 2014.
Written Opinion of the International Searching Authority, issued in PCT/JP2013/080536, dated Feb. 25, 2014.

* cited by examiner

METHOD FOR MANUFACTURING TRANSDERMAL-ABSORPTION SHEET

CROSS-REFERENCE TO RELATED APPLICATIONS

This application is a Continuation of PCT International Application No. PCT/JP2013/080536 filed on Nov. 12, 2013, which claims priority under 35 U.S.C § 119(a) to Japanese Patent Application No. 2012-249679 filed on Nov. 13, 2012. Each of the above application(s) is hereby expressly incorporated by reference, in its entirety, into the present application.

BACKGROUND OF THE INVENTION

Field of the Invention

The present invention relates to a method for manufacturing a transdermal-absorption sheet, and in particular, to a technique for concentrating a drug at needle-like protruding portions.

Description of the Related Art

In recent years, a method has been carried out in which a chemical is injected by using a transdermal-absorption sheet provided with needle-like protruding portions having a high aspect ratio and containing a drug to insert the needle-like protruding portions into the skin. In order to allow the transdermal-absorption sheet to be used as a drug, the drug needs to be mixed into the sheet. Many drugs are expensive, and thus, the drug needs to be contained in the sheet so as to concentrate at the needle-like protruding portions.

As a method for manufacturing a transdermal-absorption sheet, a method is known in which a polymer solution or the like is poured into a mold on which needle-like recessed portions that are inverted shapes of needle-like protruding portions are formed, to transfer the shapes. For example, Japanese Patent Application Laid-Open No. 2011-078617 (PTL 1) discloses use of a stamper for microneedle sheets in which through-holes penetrating a parent material are made at the bottoms of the recessed portions. PTL 1 discloses a method of first coating a surface of the stamper with a solution of a diluted drug, subsequently scraping off extra solution using a squeegee or the like, drying the drug solution, and then coating the dried drug solution with a needle raw material.

Furthermore, Japanese Patent Application Laid-Open No. 2009-195583 (PTL 2) discloses a method for manufacturing a sheet in which microneedle-like protrusions are accumulated. In the method, the sheet can be accurately manufactured in one step by filling a flexible substrate with a thick liquid consisting of a mixture of a target substance and a base utilizing a centrifugal force, while drying and hardening the liquid.

SUMMARY OF THE INVENTION

In the method in PTL 1, the drug solution is applied to the stamper, and the extra solution is scraped off using the squeegee or the like. Thus, the drug solution which is applied to the areas other than the recessed portions is not used to fill the recessed portions, leading to a loss in drug solution.

The method in PTL 2 utilizes the centrifugal force and is thus not a continuous process but is a batch process. Consequently, the method in PTL 2 does not achieve high production efficiency.

In view of these circumstances, the present invention aims to provide a method which enables a drug to be concentrated at needle-like protruding portions and which further allows transdermal-absorption sheets to be manufactured at high production efficiency.

A method for manufacturing a transdermal-absorption sheet according to an aspect of the present invention is for manufacturing a transdermal-absorption sheet with needle-like protruding portions each including a drug-containing layer and a non-drug-containing layer, the method including: a step of preparing a mold with two-dimensionally arranged needle-like recessed portions and a liquid feeding apparatus comprising a nozzle with an opening; a step of filling the two-dimensionally arranged needle-like recessed portions with a drug-containing solution by repeating a filling step of feeding the drug-containing solution from the liquid feeding apparatus to the mold and filling one or more of the needle-like recessed portions with the drug-containing solution through the nozzle aligned over the needle-like recessed portions in a state where the nozzle and a front surface of the mold are brought in contact with each other, and a moving step of moving the liquid feeding apparatus relative to the mold in a state where the nozzle and the front surface of the mold are brought in contact with each other; a step of forming a polymer sheet provided with needle-like protruding portions on a surface of the polymer sheet, the needle-like protruding portions each comprising a drug-containing layer composed of the drug-containing solution and a non-drug-containing layer composed of a non-drug-containing solution and having an inverted shape of the needle-like recessed portion; and a step of peeling the polymer sheet off from the mold.

Preferably, in the filling step, the two-dimensionally arranged needle-like recessed portions are filled with the drug-containing solution so that filling is performed on one line or a plurality of lines at a time.

Preferably, the filling step includes pressurizing an inside of the nozzle.

Preferably, in the filling step, a pressing force with which the nozzle and the mold are brought into contact with each other is equal to or stronger than a pressurizing force inside the nozzle.

Preferably, the filling step includes sucking a back surface of the mold with a reduced pressure.

Preferably, the pressing force with which the nozzle and the mold are brought into contact with each other in the filling step is stronger than a pressing force with which the nozzle and the mold are brought into contact with each other in the moving step.

Preferably, in the moving step, feeding of the drug-containing solution from the liquid feeding apparatus to the mold is stopped while the nozzle is positioned over an area other than the needle-like recessed portions in the mold.

Preferably, in the moving step, feeding of the drug-containing solution from the liquid feeding apparatus to the mold is started before the nozzle is positioned over the needle-like recessed portions, and the feeding of the drug-containing solution to the mold is stopped before the nozzle is positioned over the area other than the needle-like recessed portions in the mold.

Preferably, at least one of the nozzle and the front surface of the mold is made of an elastically deformable raw material.

Preferably, the mold comprises an air vent hole at a tip of each of the needle-like recessed portions.

Preferably, the step of forming the polymer sheet comprises a step of feeding the non-drug-containing solution to the mold with the needle-like recessed portions filled with the drug-containing solution, and then drying and solidifying the drug-containing solution and the non-drug-containing solution to form the drug-containing layer and the non-drug-containing layer.

Preferably, the step of forming the polymer sheet comprises a step of drying and solidifying the drug-containing solution filled in the needle-like recessed portions in the mold to form the drug-containing layer, feeding the non-drug-containing solution to the mold in which the drug-containing layer is formed in the needle-like recessed portions, and then drying and solidifying the non-drug-containing solution to form the non-drug containing layer.

Preferably, the step of forming the polymer sheet comprises a step of applying the non-drug-containing solution onto a surface of another support, attaching the another support onto which the non-drug-containing solution is applied to the mold with the needle-like recessed portions filled with the drug-containing solution, and drying and solidifying the drug-containing solution and the non-drug-containing solution to form the drug-containing layer and the non-drug-containing layer.

Preferably, the step of forming the polymer sheet comprises performing at least one of pressurization from the front surface of the mold and reduced pressure suction from the back surface of the mold, when drying and solidifying the drug-containing solution contained in the needle-like recessed portions in the mold.

Preferably, the step of forming the polymer sheet comprises performing at least one of pressurization of the non-drug-containing solution from a front surface of the mold and reduced pressure suction of the non-drug-containing solution from a back surface of the mold.

Preferably, the drug is peptide, protein, nucleic acid, polysaccharide, a vaccine, a medical compound belonging to a water-soluble low-molecular-weight compound, or a cosmetic component.

Preferably, the needle-like protruding portion contains the drug and hydroxyethyl starch in a tip thereof, and contains hydroxyethyl starch and hyaluronic acid in a base thereof.

Preferably, the needle-like protruding portion contains the drug and chondroitin sulfate in the tip thereof, and contains hydroxyethyl starch in the base thereof.

Preferably, the needle-like protruding portions comprise the drug-containing layer and the non-drug-containing layer, the drug-containing layer further contains hydroxyethyl starch, and the non-drug-containing layer contains hydroxyethyl starch and hyaluronic acid.

Preferably, the needle-like protruding portions comprise the drug-containing layer and the non-drug-containing layer, the drug-containing layer further contains chondroitin sulfate, and the non-drug-containing layer contains hydroxyethyl starch.

According to the present invention, a transdermal-absorption sheet can be efficiently manufactured which allows a drug to be eccentrically located in needle-like protruding portions.

DETAILED DESCRIPTION OF THE EMBODIMENTS

Figure 1A:
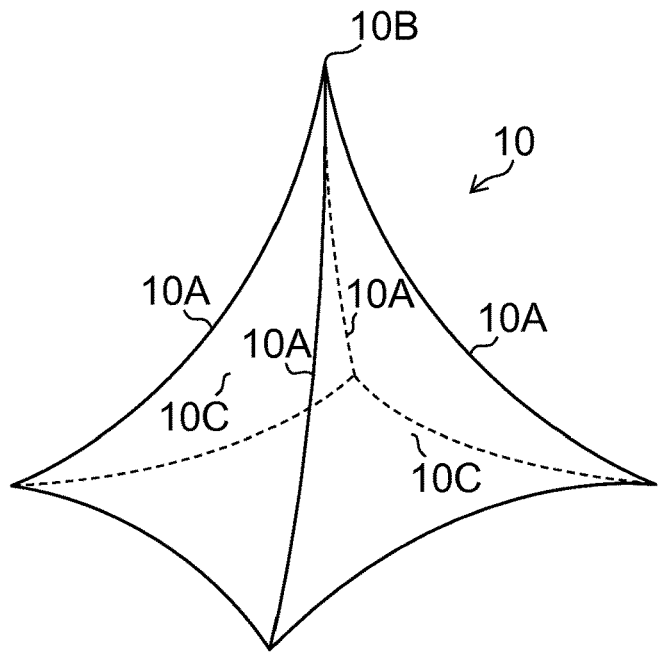
FIG. 1A is a perspective view of a pyramidal microneedle (needle-like protruding portion) on a transdermal-absorption sheet.

A preferred embodiment of the present invention is described below in accordance with the accompanying drawings. The present invention is described using the following preferred embodiment. However, many techniques may be used to vary the embodiment without departing from the scope of the present invention, and embodiments other than the present embodiment may be utilized. Thus, all the variations within the scope of the present invention are included in the claims.

In the figures, components designated by the same reference numeral are similar components with similar functions. Furthermore, in the present specification, when a numerical range is described using "to", numerical values for an upper limit and a lower limit illustrated with "to" are also included in the numerical range.

Taking, as an example, a transdermal-absorption sheet with needle-like protruding portions arranged in an array according to the embodiment of the present invention, a method for manufacturing the transdermal-absorption sheet is described. The transdermal-absorption sheet is described, but the present invention may be applied to a functional film other than the transdermal-absorption sheet which has a needle-like protruding portions arranged in an array.

Figure 1B:
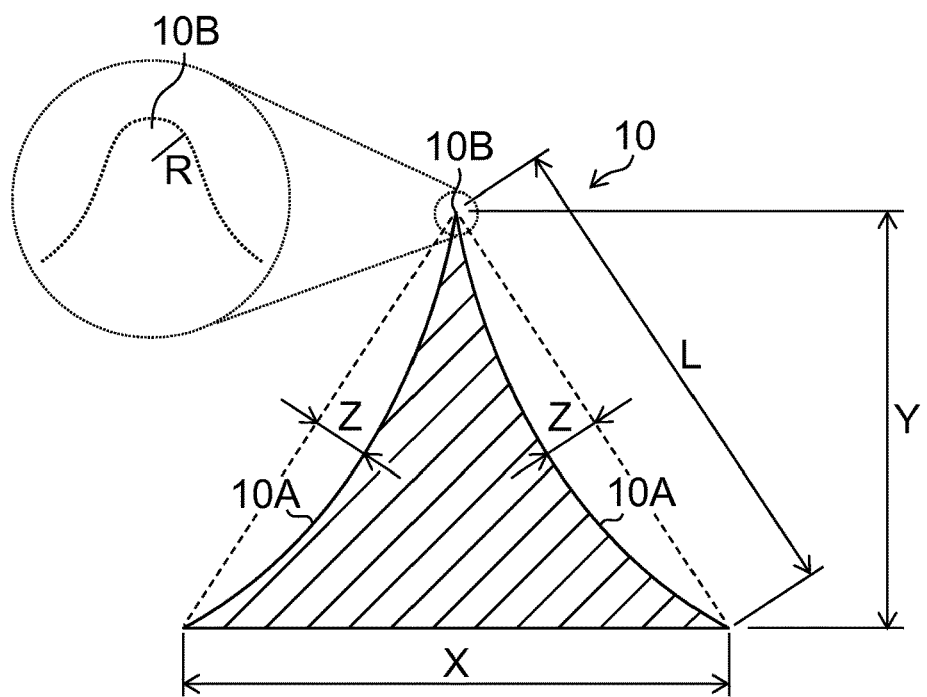
FIG. 1B is a cross-sectional view of the pyramidal microneedle (needle-like protruding portion) on the transdermal-absorption sheet.

With reference to FIGS. 1A and 1B, needle-like protruding portions (also referred to as microneedles) on a transdermal-absorption sheet are described which sheet is manufactured by a method for manufacturing a transdermal-absorption sheet according to the embodiment of the present invention. In the present embodiment, an example of quadrangular pyramidal needle-like protruding portions is described, however, the present invention is not limited to this shape.

As depicted in a perspective view in FIG. 1A and a cross-sectional view in FIG. 1B, the microneedle (needle-like protruding portion) 10 formed on the transdermal-absorption sheet needs to be shaped as follows so as to be stuck several hundred vm deep into the surface of the skin: (1) The tip is sufficiently pointed, and the diameter of the needle penetrating the skin is sufficiently small (the aspect ratio of length/diameter is high), and (2) the microneedle has a sufficient strength (the needle does not bend).

Thus, to meet the requirement in (1), a thin and pointed shape is needed. However, this is opposed to (2), and an excessively thin needle is bent at the tip or root thereof, whereas an excessively thick needle fails to be stuck into the skin Thus, as depicted in FIG. 1A, a ridge line 10A of the microneedle 10 is preferably shaped to be curved toward the inside of the microneedle. The microneedle with such a shape can be made difficult to bend by sufficiently sharpening the tip, while widening the root. Furthermore, the ridge lines 10A, 10A of a quadrangular pyramidal microneedle preferably extend from a quadrangular pyramidal surface 10C between the ridge lines.

The shape of the microneedle 10 is preferably such that a bottom surface is within the range of 0.1 μm or more and 1,000 μm or less on a side X, and 0.3 μm or more and 3,000 μm or less in height. More preferably, the bottom surface is within the range of 10 μm or more and 400 μm or less on a side X, and 30 μm or more and 1,200 μm or less in height.

When the length of a segment connecting a start point and an end point of the ridge line is represented as L, the maximum depth Z of curve of the ridge line 10A is preferably 0.04×L or more and 0.2×L or less. Furthermore, the radius of curvature R of a tip 10B of the microneedle, which indicates sharpness of the microneedle 10, is preferably 20 μm or less, and more preferably 15 μm or less.

Figure 2A:
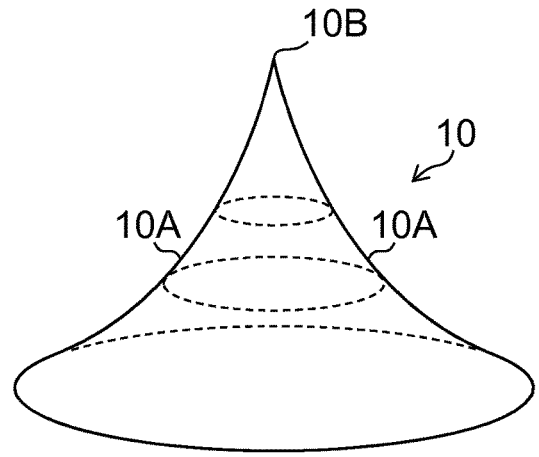
FIG. 2A is a perspective view of a conical microneedle (needle-like protruding portion) on the transdermal-absorption sheet.
Figure 2B:
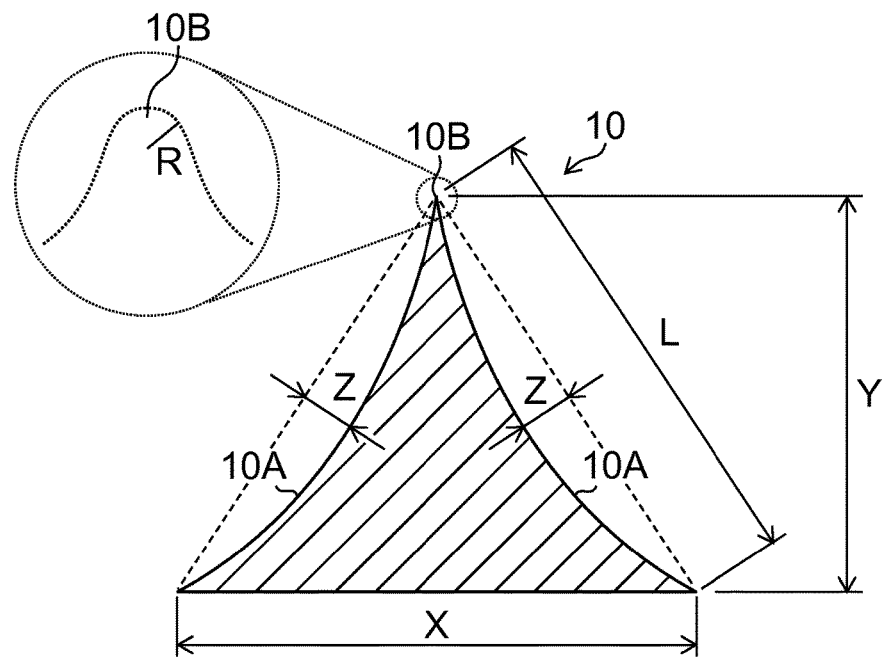
FIG. 2B is a cross-sectional view of the conical microneedle (needle-like protruding portion) on the transdermal-absorption sheet.

FIGS. 1A and 1B depict the quadrangular pyramidal microneedle 10. However, a conical microneedle depicted in FIGS. 2A and 2B and microneedles having other pyramids such as a triangular pyramid preferably have similar sizes. For the cone, the diameter X of the bottom surface is preferably within the range of 0.1 μm or more and 1,000 μm or less, and more preferably within the range of 50 μm or more and 500 μm or less. Furthermore, when the length of a segment connecting a start point and an end point of generatrix of the conical surface is represented as L, the maximum depth Z of curve of the conical surface is preferably 0.04×L or more and 0.2×L or less.

As described above, the transdermal-absorption sheet forms a protruding portion array in which the microneedles are arranged in a two-dimensional array. In order to allow the microneedle to be easily stuck into the surface of the skin, it is important to sufficiently sharpen the microneedle tip 10B. The radius of curvature R of the tip 10B of the microneedle is preferably 20 μm or less. In forming a microneedle 10 having a tip with a radius of curvature R of 20 μm or less, an important point is whether a solution of a polymer resin can be injected down to the tip (bottom) of a needle-like recessed portion corresponding to an inverted shape of the protrusion array formed in the mold to allow accurate transfer.

Furthermore, the transdermal-absorption sheet needs to contain a drug, but many drugs are expensive. Thus, it is economically important to contain the drug in the transdermal-absorption sheet so that the drug concentrates at the portion of each microneedle.

[Method for Manufacturing the Transdermal-Absorption Sheet]

Now, a method for manufacturing the transdermal-absorption sheet according to the embodiment of the present invention is described.

(Production of the Mold)

Figure 3A:
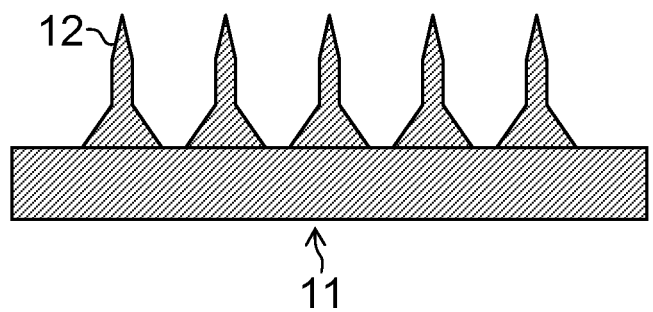
FIG. 3A is a process diagram of a method for manufacturing a mold.
Figure 3B:
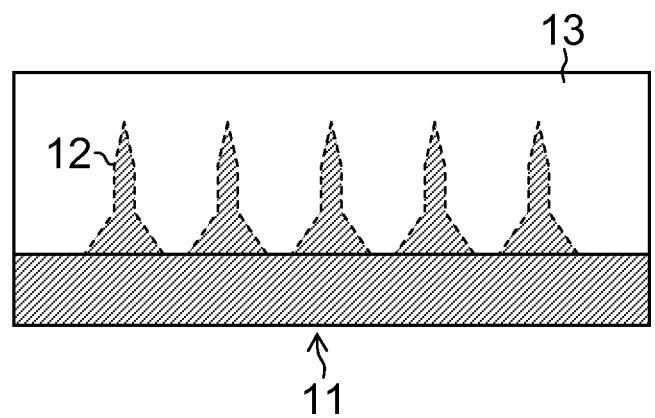
FIG. 3B is a process diagram of the method for manufacturing the mold.
Figure 3C:
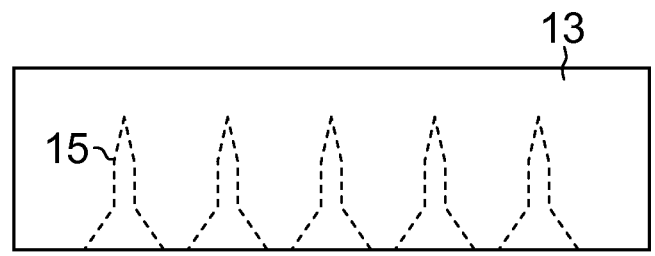
FIG. 3C is a process diagram of the method for manufacturing the mold.

FIGS. 3A to 3C are process diagrams illustrating production of a mold.

As depicted in FIG. 3A, an original plate is first produced which is used to produce a mold that allows the transdermal-absorption sheet to be manufactured.

Two types of methods for producing an original plate 11 are available. A first method is to apply a photo resist to an Si substrate and then to expose and develop the photo resist. Then, etching such as RIE (Reactive Ion Etching) is performed on the photo resist to form an array of conical shape portions (protruding portions) 12 on a surface of the original plate 11. When etching such as RIE is performed so as to form the conical shape portions on the surface of the original plate 11, the conical shapes can be formed by carrying out the etching in an oblique direction while the Si substrate is being rotated.

A second method is a method of machining a metal substrate such as Ni using a cutting tool such as a diamond byte to form an array of the shape portions 12 shaped like quadrangular pyramids or the like on the surface of the original plate 11.

Then, the mold is produced. Specifically, as depicted in FIG. 3B, the mold 13 is produced from the original plate 11. A method using Ni electrocasting or the like is generally employed for production of the mold 13. Since the original plate 11 has the shape of cones or pyramids (such as quadrangular pyramids) with pointed tips, four methods are conceived which enables to precisely transfer the shape of the original plate 11 to the mold 13 and then to peel off the mold 13 from the original plate 11, while manufacturing the mold 13 at low cost.

A first method is a method of pouring, into the original plate 11, a silicone resin containing PDMS (polydimethylcyloxane, for example, Sylgard 184 (registered trademark) manufactured by Dow Corning Toray Co., Ltd.) with a curing agent added thereto, heating and curing the silicone resin at 100° C., and then peeling the silicon resin off from the original plate 11. A second method is a method of pouring, into the original plate 11, a UV (ultraviolet) curing resin that is curable by irradiation of ultraviolet light, irradiating the UV curing resin with ultraviolet light in a nitrogen atmosphere, and then peeling the UV curing resin off from the original plate 11. A third method is a method of pouring a solution of a plastic resin such as polystyrene or PMMA (polymethylmetacrylate) dissolved into an organic solvent, into the original plate 11 coated with a release agent, volatilizing the organic solvent by means of drying to cure the plastic resin, and then peeling the plastic resin off from the original plate 11. A fourth method is a method of producing an inverted structure by means of Ni electrocasting.

Thus, the mold 13 is produced in which needle-like recessed portions 15 that are inverted shapes of cones or pyramids on the original plate 11 are arranged in a two-dimensional array. The mold 13 produced as described above is depicted in FIG. 3C. The mold 13 can be easily produced any number of times using any of the above-described four methods. Then, a frame 14 is installed on the mold 13 manufactured in FIG. 3C.

Figure 4A:
FIG. 4A is a front view of a mold provided with a frame.
Figure 4B:
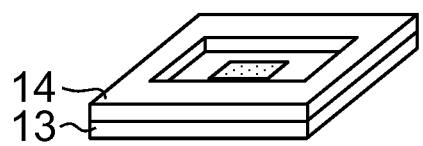
FIG. 4B is a perspective view of the mold provided with the frame.
Figure 4C:
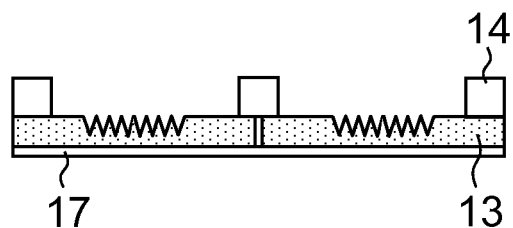
FIG. 4C is a front view of the mold provided with the frame.
Figure 4D:
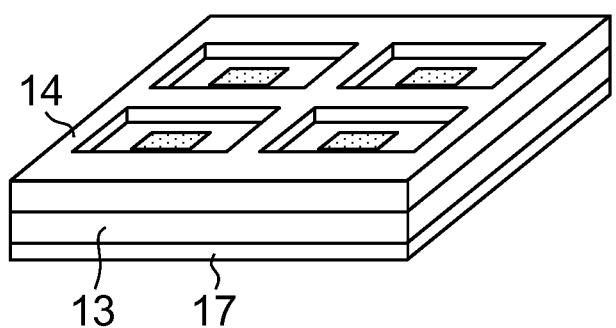
FIG. 4D is a perspective view of the mold provided with the frame.

FIGS. 4A to 4D are diagrams depicting that the frame 14 is installed on the mold. FIGS. 4A and 4B are a plan view and a perspective view of a case where the frame is provided at the periphery of the mold 13, respectively. FIGS. 4C and 4D are a plan view and a perspective view of a case where a plurality of molds 13 are joined together and the frame 14 is also provided inside the mold, respectively. Provision of the frame 14 allows a solution of a polymer resin (hereinafter also referred to as a "polymer solution") to be prevented from flowing out from the mold 13 when the functional film is formed to a desired film thickness.

At this time, a step (level difference) between the mold 13 and the frame 14 is preferably 50 μm or more and 10 mm or less. Furthermore, the molds in FIGS. 4A to 4D are configured to enable the mold 13 and the frame 14 to be separated from each other, but the mold 13 and the frame 14 may be integrated together. When the mold 13 and the frame 14 are configured to be separable, the frame 14 can be removed in a drying step and a peeling-off step following the filling step.

In FIGS. 4C and 4D, a plurality of molds 13 are joined onto a substrate 17 and the plurality of molds 13 are joined to one another, using an adhesive. Then, the frame 14 is installed at the periphery of a side surface of the mold 13 and inside the mold 13.

Figure 5:
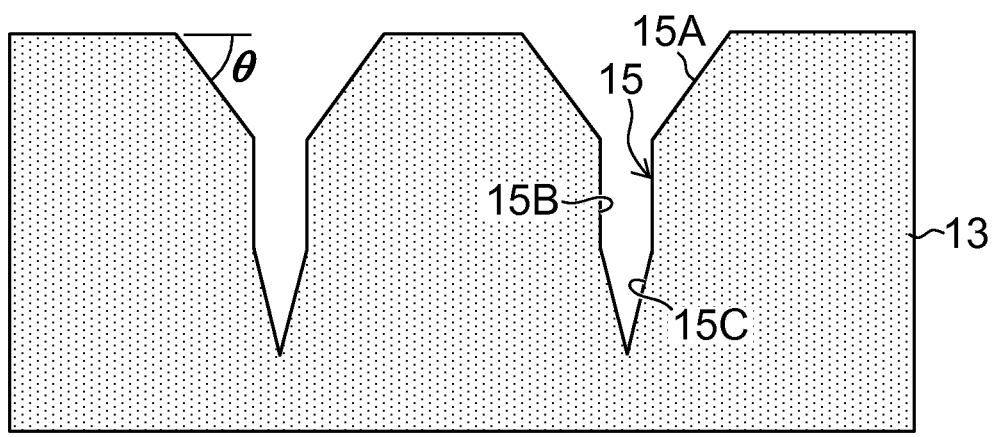
FIG. 5 is a cross-sectional view depicting a mold in another embodiment.

FIG. 5 depicts an embodiment of another preferred mold 13. A needle-like recessed portion 15 includes a tapered inlet portion 15A that is narrower in a depth direction from the front surface of the mold 13, an intermediate recessed portion 15B with a constant width in the depth direction, and a tip recessed portion 15C that is tapered in the depth direction. The angle θ of the taper is desirably within the range of 10° to 20°. The tapered inlet portion 15A allows the needle-like recessed portion 15 to be easily filled with the polymer solution.

Figure 6:
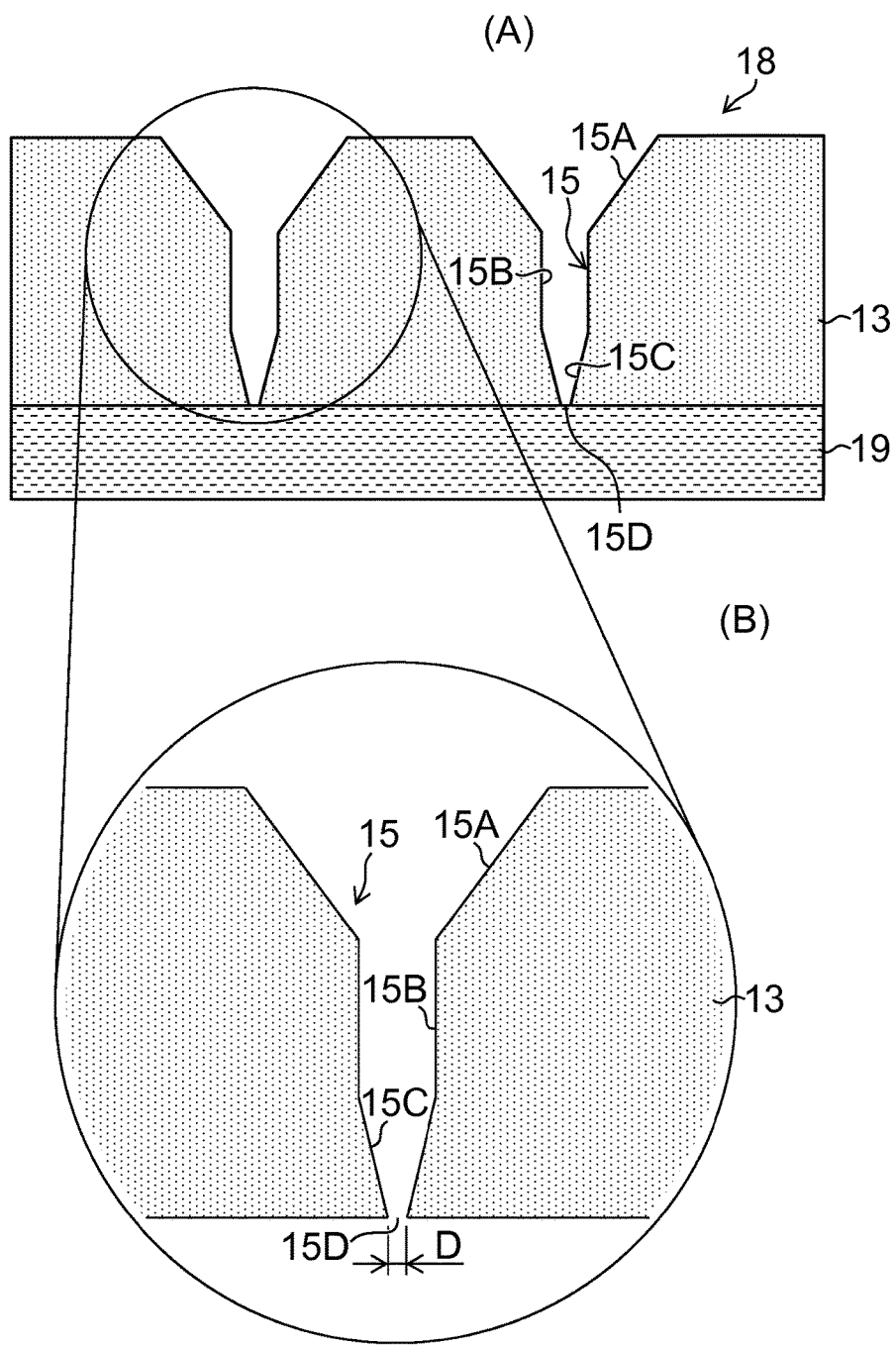
FIG. 6 is a cross-sectional view depicting a mold complex.

FIG. 6 depicts an embodiment of a mold complex 18 that is more preferable in executing the method for manufacturing the transdermal-absorption sheet. Portion (A) of FIG. 6 depicts the mold complex 18. Portion (B) of FIG. 6 is an enlarged view of a circled portion in portion (A).

As depicted in portion (A) of FIG. 6, the mold complex 18 includes the mold 13 in which an air vent hole 15D is formed at the tip (bottom) of each needle-like recessed portion 15 and a gas permeable sheet 19 laminated to a back surface of the mold 13 and formed of a material that allows gas to permeate, while preventing liquid from permeating. The air vent hole 15D is formed as a through-hole that penetrates the back surface of the mold 13. In this regard, the back surface of the mold 13 refers to a surface on the side of the mold 13 on which the air vent hole 15D is formed. Thus, a tip of the needle-like recessed portion 15 communicates with the atmosphere via the air vent hole 15D and the gas permeable sheet 19.

The use of the mold complex 18 as described above allows only the air present in the needle-like recessed portions 15 to be driven out from the needle-like recessed portions 15 while preventing permeation of the transdermal-absorption material solution filled in the needle-like recessed portions 15. This improves transferability with which the shape of the needle-like recessed portions 15 is transferred to the transdermal-absorption material and allows formation of sharper microneedles 10.

The diameter D (diameter) of the air vent hole 15D is preferably within the range of 1 to 50 μm. A diameter D of the air vent hole 15D of less than 1 μm fails to allow the air vent hole to sufficiently accomplish the functions thereof. A diameter D of the air vent hole 15D of more than 50 μm is likely to cause the sharpness of the tip of the molded microneedle 10 to be degraded.

As a gas permeable sheet 19 formed of a material that allows gas to permeate while preventing liquid from permeating, for example, latex (Asahi Kasei Chemicals Corporation) may be suitably used.

As a material used for the mold 13, an elastic raw material and a metallic raw material may be used. In particular, the elastic raw material is preferable and a raw material with high gas permeability is more preferable. The oxygen permeability, which is representative of the gas permeability, is preferably more than $1 \times 10^{-12}$ (mL/s·m²·Pa) and more preferably more than $1 \times 10^{-10}$ (mL/s·m²·Pa). Setting the gas permeability to within the above-described range allows the air present in the recessed portions in the mold 13 to be driven out from the mold side, allowing manufacture of microarray needles with few defects. Specifically, examples of such raw material include materials obtained by melting a silicone resin (for example, Sylgard 184 (registered trademark) manufactured by Dow Corning Toray Co., Ltd. or KE-1310ST (product number) manufactured by Shin-Etsu Chemical Co., Ltd.), a UV curing resin, or a plastic resin (for example, polystyrene or PMMA (polymethylmethacrylate)), and materials obtained by dissolving any of above resins into a solvent. Among these materials, silicone rubber-based materials can be suitably used because of the durability thereof against transfers using repeated pressurization and the good peelability thereof from the raw material. Furthermore, examples of the metallic raw material include Ni, Cu, Cr, Mo, W, Ir, Tr, Fe, Co, MgO, Ti, Zr, Hf, V, Nb, Ta, α-aluminum oxide, zirconium oxide, stainless steel (for example, a STAVAX (trademark) material manufactured by Bohler-Uddeholm KK), and alloys thereof. For the material of the frame 14, a material similar to the material of the mold 13 may be used.

(Polymer Solution)

The polymer solution that is a solution of the polymer resin used for the present embodiment is described.

Preferably, a biocompatible resin is used as a raw material for the resin polymer used for the polymer solution. It is preferable to use, as such a resin, sugar such as glucose, maltose, pullulan, chondroitin sulfate, sodium hyaluronate, hydroxypropyl cellulose, or hydroxyethyl starch, protein such as gelatin, polylactate, or a biodegradable polymer such as a lactic acid-glycollic acid copolymer. Among these resins, a gelatin-based materials have an adhesion with many base materials and have a high gel strength as materials to be gelated. Thus, the gelatin-based materials can be suitably used during a peeling-off step described below because the materials can be brought into tight contact with the base material to allow the functional film to be peeled off from the mold using the base material. The density of the resin is preferably such that 10 to 50% resin polymer is contained in the solution, though the density depends on the type of the material. Additionally, a solvent used for dissolution may be other than hot water as long as the solvent has volatility, and methylethylketone (MEK), alcohol, or the like may be used. A drug to be supplied to the inside of the human body may concurrently be dissolved into a solution of the polymer resin in accordance with the application.

For a method for preparing the polymer solution, when a water-soluble polymer (gelatin or the like) is used, the solution can be prepared by dissolving water-soluble powder into water, and after the dissolution, adding a chemical to the solution. If the material is difficult to dissolve into water, the material may be dissolved on heating. The temperature may be selected as needed depending on the type of the polymer material, but the material is preferably heated at approximately 60° C. or less. Furthermore, when a thermally melted polymer (maltose or the like) is used, the solution can be prepared by melting the raw material and the chemical on heating. The heating temperature is preferably a temperature at which the raw material is melted, and is specifically approximately 150° C.

In the present embodiment, the polymer solution containing the drug is referred to as the drug-containing solution, and the polymer solution containing no drug is referred to as the non-drug-containing solution, as needed.

The viscosity of the solution of the polymer resin is preferably 100 Pa·s or less, and more preferably 10 Pa·s or less for the drug-containing solution. The viscosity of the solution of the polymer resin is preferably 2,000 Pa·s or less, and more preferably 1,000 Pa·s or less for the non-drug-containing solution. Appropriate adjustment of the viscosity of the solution of the polymer resin facilitates injection of the solution into the recessed portions of the mold.

(Drug)

The drug contained in the polymer solution is not limited as long as the drug has the functions of a drug. In particular, the drug is preferably selected from the group consisting of peptide, protein, nucleic acid, polysaccharide, a vaccine, a medical compound belonging to a water-soluble low-molecular-weight compound, and a cosmetic component. As the water-soluble polymer substance contained in the drug-containing layer, one that does not interact with the drug contained in the layer is preferably used. For example, if protein is used as the drug, when a chargeable polymer substance is mixed with the protein, the protein and the polymer substance electrostatically interact with each other to form an aggregate, which is cohered and precipitated. Therefore, when a chargeable substance is used in the drug, a water-soluble polymer substance with no charge such as hydroxyethyl starch or dextran is preferably used.

<Manufacture of the Transdermal-Absorption Sheet>

Figure 7A:
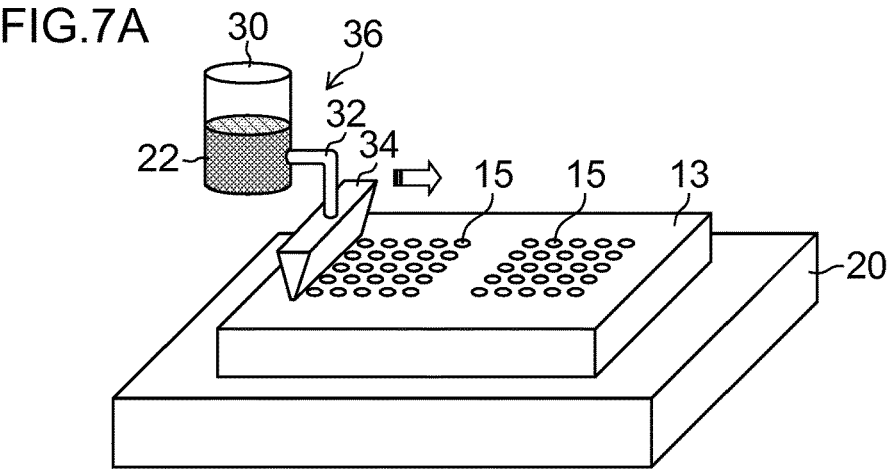
FIG. 7A is a schematic diagram depicting a step of filling the mold with a drug-containing solution.

A method for manufacturing the transdermal-absorption sheet using the mold 13 manufactured as described above is described. As depicted in FIG. 7A, the mold 13 with the two-dimensionally arranged needle-like recessed portions 15 is placed on a base 20. Two sets of a plurality of needle-like recessed portions 15, each set including 5×5 two-dimensionally arranged needle-like recessed portions 15, are formed in the mold 13. A liquid feeding apparatus 36 is prepared which has a tank 30 housing a drug-containing solution 22, a pipe 32 connected to the tank, and a nozzle 34 connected to a tip of the pipe 32.

Figure 8:
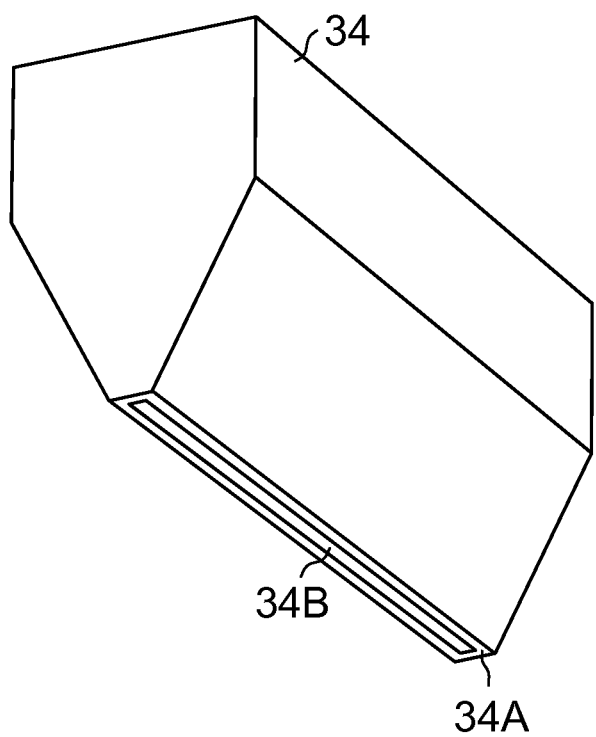
FIG. 8 is a perspective view depicting a tip of a nozzle.

FIG. 8 depicts a schematic perspective view of the tip of the nozzle. As depicted in FIG. 8, the tip of the nozzle 34 includes a lip portion 34A that is a flat surface and a slit-shaped opening 34B. The slit-shaped opening 34B, for example, allows a plurality of needle-like recessed portions 15 constituting one line to be simultaneously filled with the drug-containing solution 22. The size (length and width) of the opening 34B is selected as needed in accordance with the number of needle-like recessed portions 15 to be filled at a time.

An increased length of the opening 34B allows an increased number of needle-like recessed portions 15 to be filled at a time with the drug-containing solution 22. Thus, productivity can be improved.

Figure 9:
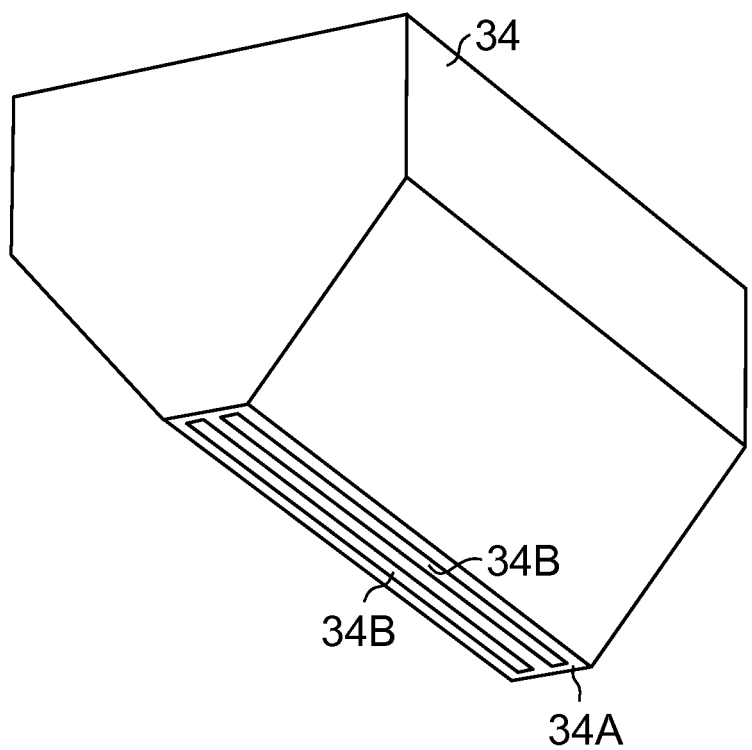
FIG. 9 is a perspective view depicting a tip of another nozzle.

FIG. 9 depicts a schematic perspective view of a tip of another nozzle. As depicted in FIG. 9, the lip portion 34A at the tip of the nozzle 34 has two slit-shaped openings 34B. The two openings 34B, for example, allow a plurality of needle-like recessed portions 15 constituting two lines to be simultaneously filled with the drug-containing solution 22.

As a material used for the nozzle 34, an elastic raw material and a metallic raw material may be used. For example, Teflon (registered trademark), stainless steel (SUS), or titanium may be used.

Figure 7B:
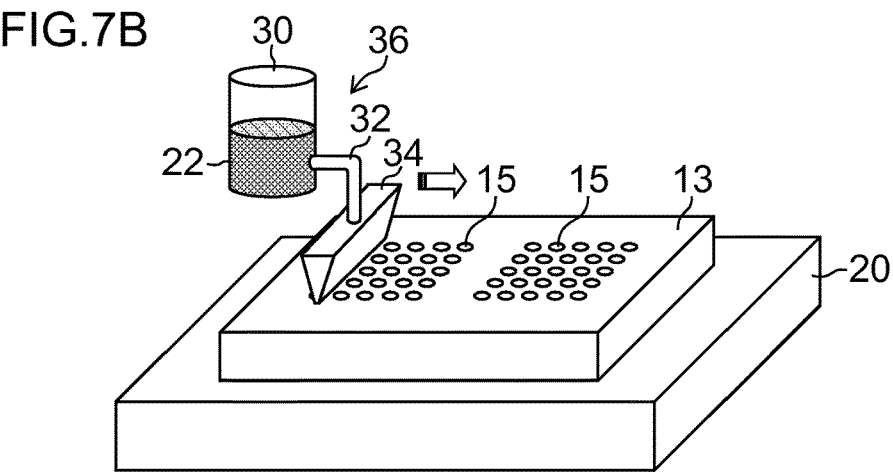
FIG. 7B is a schematic diagram depicting the step of filling the mold with the drug-containing solution.

A filling step is described with reference to FIG. 7B. As depicted in FIG. 7B, the opening 34B in the nozzle 34 is aligned over the needle-like recessed portions 15. The lip portion 34A of the nozzle 34 is in contact with the front surface of the mold 13. The drug-containing solution 22 is fed from the liquid feeding apparatus 36 to the mold 13, and the needle-like recessed portions 15 are filled with the drug-containing solution 22 through the opening 34B in the nozzle 34. In the present embodiment, a plurality of needle-like recessed portions 15 constituting one line are simultaneously filled with the drug-containing solution 22. However, the present invention is not limited to this configuration. The needle-like recessed portions 15 may be filled with the drug-containing solution 22 one by one. Furthermore, the use of the nozzle 34 depicted in FIG. 9 allows a plurality of needle-like recessed portions 15 constituting a plurality of lines to be simultaneously filled with the drug-containing solution 22 so that filling is performed on a plurality of lines at a time.

When the mold 13 is composed of a raw material having gas permeability, the drug-containing solution 22 can be sucked by sucking the back surface of the mold 13, promoting filling of the inside of the needle-like recessed portions 15 with the drug-containing solution 22.

Figure 7C:
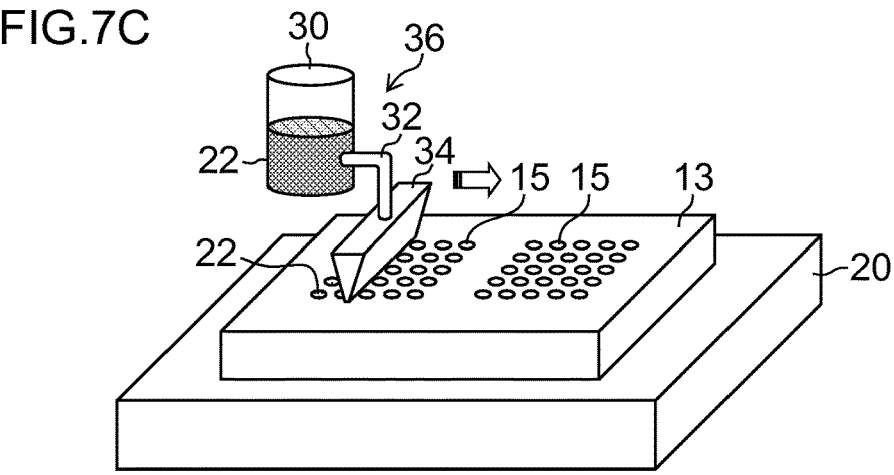
FIG. 7C is a schematic diagram depicting the step of filling the mold with the drug-containing solution.

After the filling step described with reference to FIG. 7B, with the lip portion 34A of the nozzle 34 and the front surface of the mold 13 in contact with each other, the liquid feeding apparatus 36 is relatively moved in a direction perpendicular to a length direction of the opening 34B, to move the nozzle 34 to the needle-like recessed portions 15 not filled with the drug-containing solution 22, as depicted in FIG. 7C. The opening 34B in the nozzle 34 is aligned over the needle-like recessed portions 15. The present embodiment has been described with reference to the example in which the nozzle 34 is moved. However, the mold 13 may be moved.

Since the nozzle 34 is moved with the lip portion 34A of the nozzle 34 and the front surface of the mold 13 in contact with each other, the nozzle 34 can scrape off the drug-containing solution 22 remaining on the surface of the mold 13 except on the needle-like recessed portions 15. This enables the drug-containing solution 22 to be prevented from remaining on the mold 13 except on the needle-like recessed portions 15.

In order to reduce damage to the mold 13 and to suppress deformation of the mold 13 due to compression as much as possible, the pressing pressure with which the nozzle 34 is pressed against the mold 13 at the time of movement is preferably minimized. Furthermore, in order to prevent the drug-containing solution 22 from remaining on the mold 13 except on the needle-like recessed portions 15, at least one of the mold 13 and the nozzle 34 is desirably formed of a flexible, elastically deformable raw material.

The filling step in FIG. 7B and the moving step in FIG. 7C are repeated to fill the 5×5 two-dimensionally arranged needle-like recessed portions 15 with the drug-containing solution 22. When the 5×5 two-dimensionally arranged needle-like recessed portions 15 are filled with the drug-containing solution 22, the liquid feeding apparatus 36 is moved to the adjacent 5×5 two-dimensionally arranged needle-like recessed portions 15, and the filling step in FIG. 7B and the moving step in FIG. 7C are repeated. The adjacent 5×5 two-dimensionally arranged needle-like recessed portions 15 are also filled with the drug-containing solution 22.

The above-described filling step and moving step may be in (1) a form in which the needle-like recessed portions 15 are filled with the drug-containing solution 22 while the nozzle 34 is being moved or (2) a form in which, while the nozzle 34 is in motion, the nozzle 34 is temporarily stopped over the needle-like recessed portions 15 to fill the needle-like recessed portions 15 with the drug-containing solution 22, and the nozzle 34 is moved again after the filling. Between the filling step and the moving step, the lip portion 34A of the nozzle 34 is in contact with the front surface of the mold 13.

Figure 10:
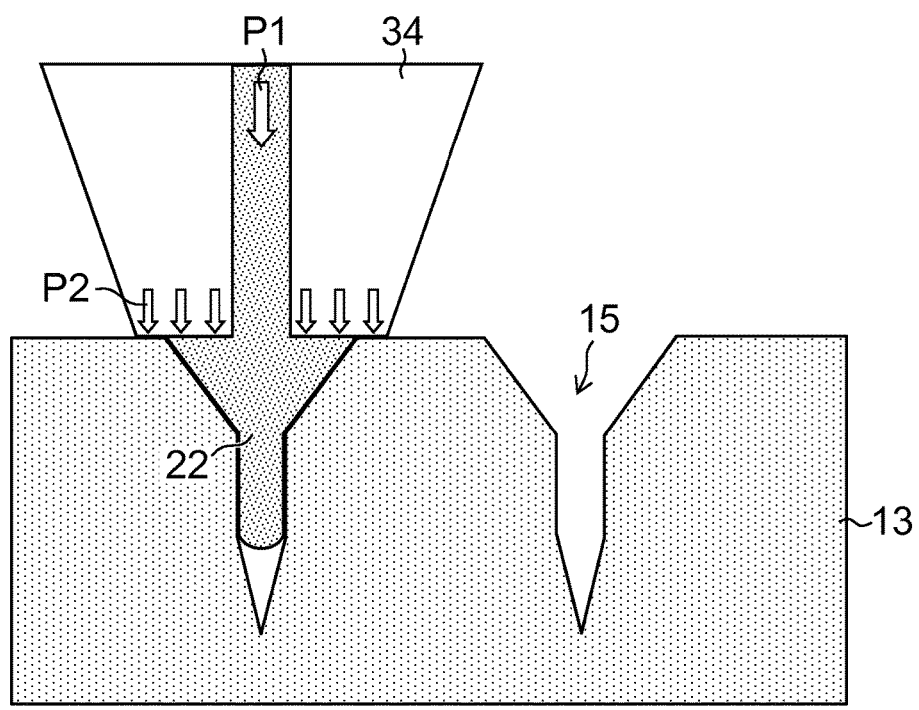
FIG. 10 is a partially enlarged view of the mold and the tip of the nozzle while filling.

FIG. 10 is a partially enlarged view of the tip of the nozzle 34 and the mold 13 during filling of the needle-like recessed portions 15 with the drug-containing solution 22. As depicted in FIG. 10, filling of the inside of the needle-like recessed portions 15 with the drug-containing solution 22 can be promoted by applying a pressuring force P1 into the nozzle 34. Moreover, when the inside of the needle-like recessed portions 15 is filled with the drug-containing solution 22, a pressing force P2 with which the nozzle 34 is brought into contact with the front surface of the mold 13 is preferably set equal to or stronger than the pressuring force P1 in the nozzle 34. Setting the pressing force P2≥the pressuring force P1 enables the drug-containing solution 22 to be restrained from leaking from the needle-like recessed portions 15 to the front surface of the mold 13.

Figure 11:
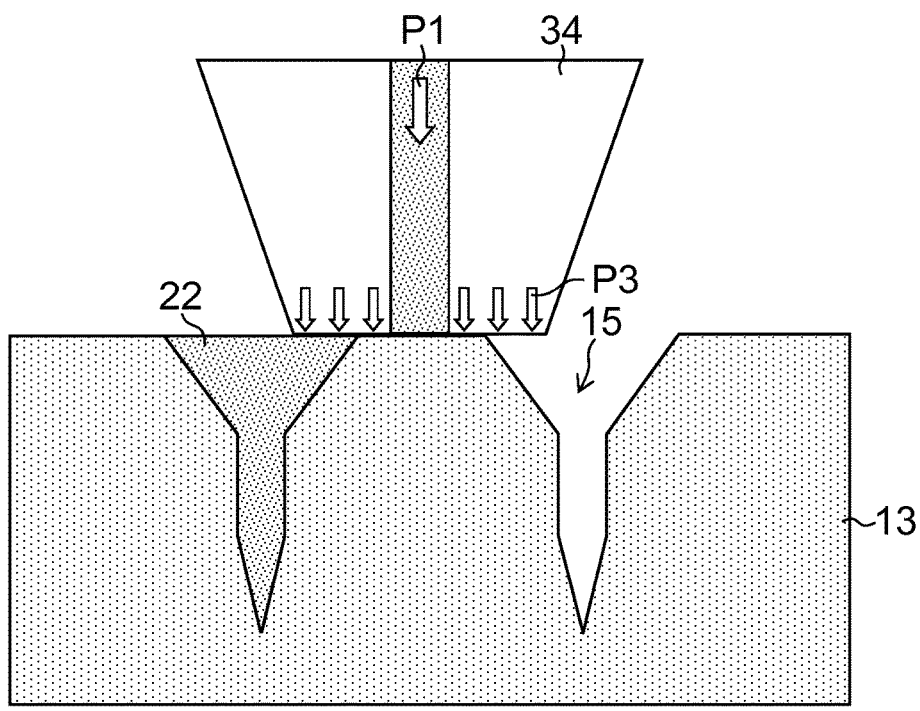
FIG. 11 is a partially enlarged view of the mold and the tip of the nozzle while moving.

FIG. 11 is a partially enlarged view of the tip of the nozzle 34 and the mold 13 during movement of the nozzle 34. When the nozzle 34 is moved relative to the mold 13, a pressing force P3 with which the nozzle 34 is brought into contact with the front surface of the mold 13 is preferably set weaker than the pressing force P2 with which the nozzle 34 is brought into contact with the front surface of the mold 13 while filling is performed. This is intended to reduce damage to the mold 13 and to suppress deformation of the mold 13 associated with compression.

Figure 12:
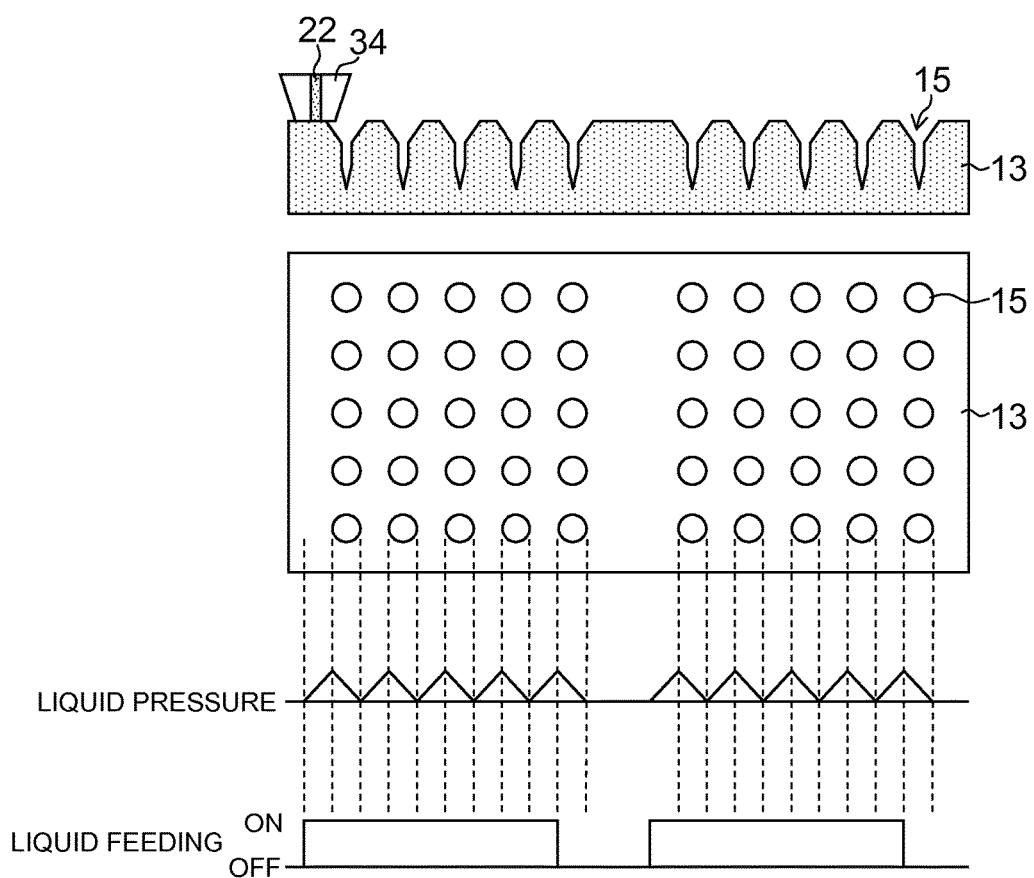
FIG. 12 is a diagram illustrating the relation between the liquid pressure in the nozzle and feeding of the drug-containing solution.

FIG. 12 is a diagram illustrating the relation between the liquid pressure in the nozzle and feeding of the drug-containing solution. As depicted in FIG. 12, feeding of the drug-containing solution 22 is started before the nozzle 34 is positioned over the needle-like recessed portions 15. This is intended to reliably fill the needle-like recessed portions 15 with the drug-containing solution 22. The drug-containing solution 22 is continuously fed to the mold 13 until the filling of the plurality of needle-like recessed portions 15 composed of the 5×5 needle-like recessed portions 15 is complete. The feeding of the drug-containing solution 22 to the mold 13 is stopped before the nozzle 34 is positioned over the fifth line of the needle-like recessed portions 15. This allows the drug-containing solution 22 to be prevented from overflowing the needle-like recessed portions 15. When the feeding of the drug-containing solution 22 is started, the liquid pressure in the nozzle 34 is elevated in areas where the nozzle 34 is not positioned over the needle-like recessed portions 15. On the other hand, when the nozzle 34 is positioned over the needle-like recessed portions 15, the needle-like recessed portions 15 are filled with the drug-containing solution 22 to lower the liquid pressure in the nozzle 34. The variation in liquid pressure is repeated.

When the filling of the plurality of needle-like recessed portions 15 composed of the 5×5 needle-like recessed portions 15 is complete, the nozzle 34 is moved to the adjacent plurality of needle-like recessed portions 15 composed of the 5×5 needle-like recessed portions 15. For the liquid feeding, the feeding of the drug-containing solution 22 is preferably stopped at the time of movement to the adjacent plurality of needle-like recessed portions 15 composed of the 5×5 needle-like recessed portions 15. A long distance is present between the fifth line of needle-like recessed portions 15 and the next first line of needle-like recessed portions 15. When the drug-containing solution 22 is continuously fed while the nozzle 34 is moving between the fifth line of needle-like recessed portions 15 and the next first line of needle-like recessed portions 15, the liquid pressure in the nozzle 34 may be excessively high. As a result, the drug-containing solution 22 may flow out from the nozzle 34 onto an area other than the needle-like recessed portions 15 in the mold 13. In order to inhibit this, preferably, the liquid pressure in the nozzle 34 is detected so that the feeding of the drug-containing solution 22 is stopped upon determining that the liquid pressure is to be excessively high.

When the filling of the needle-like recessed portions 15 with the drug-containing solution 22 is complete, the process proceeds to a step of forming a polymer sheet with needle-like protruding portions each formed on a surface of the sheet, the polymer sheet including a drug-containing layer composed of the drug-containing solution 22 and a non-drug-containing layer composed of a non-drug-containing solution. The needle-like protruding portions have inverted shapes of the needle-like recessed portions.

Figure 13A:
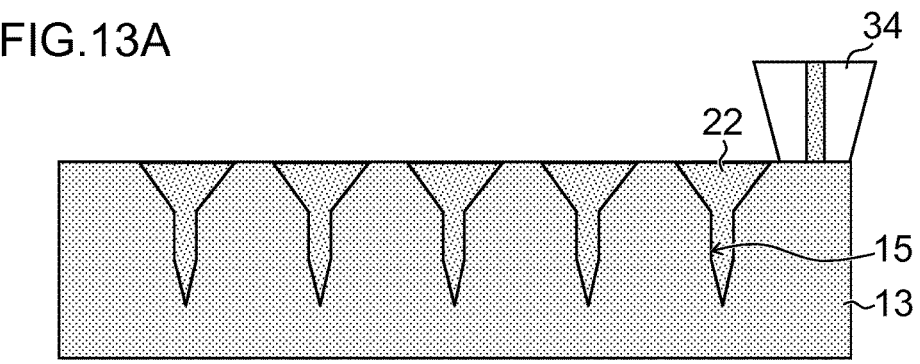
FIG. 13A is a diagram illustrating a process of forming a polymer sheet.
Figure 13B:
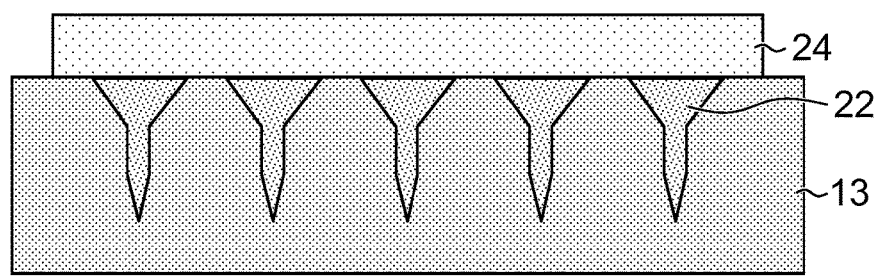
FIG. 13B is a diagram illustrating the process of forming the polymer sheet.

Several aspects of the process of forming the polymer sheet are described. A first aspect is described with reference to FIGS. 13A to 13C. As depicted in FIG. 13A, the needle-like recessed portions 15 in the mold 13 are filled with the drug-containing solution 22 through the nozzle 34. Then, as depicted in FIG. 13B, a non-drug-containing solution 24 is applied onto a surface of the drug-containing solution 22 using a dispenser. In addition to the application using the dispenser, for example, a bar coating method, a spin coating method, and an application using a spray or the like are applicable.

Figure 13C:
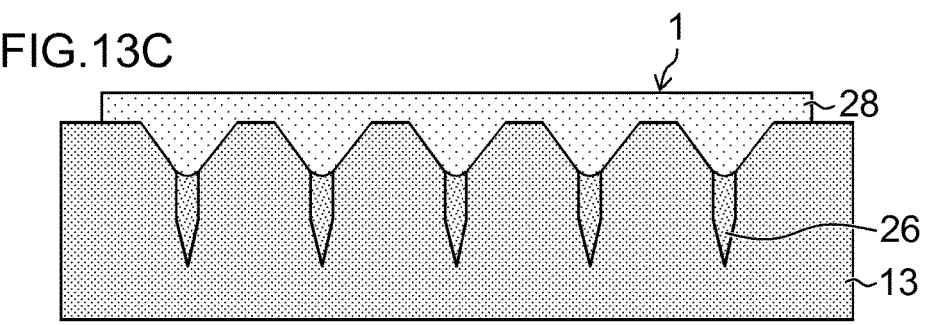
FIG. 13C is a diagram illustrating the process of forming the polymer sheet.

Then, as depicted in FIG. 13C, the drug-containing solution 22 and the non-drug-containing solution 24 are dried and solidified to form a polymer sheet 1 including a drug-containing layer 26 and a non-drug-containing layer 28.

In the first embodiment, pressurization from the front surface of the mold 13 and reduced pressure suction (vacuum suction) from the back surface of the mold 13 may be preferably performed in order to promote filling of the inside of the needle-like recessed portions 15 with the drug-containing solution 22 and the non-drug-containing solution 24.

Figure 14A:
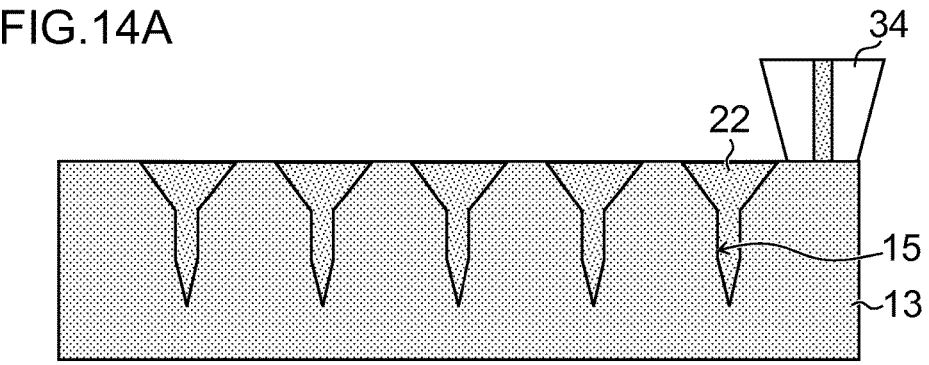
FIG. 14A is a diagram illustrating another process of forming the polymer sheet.
Figure 14B:
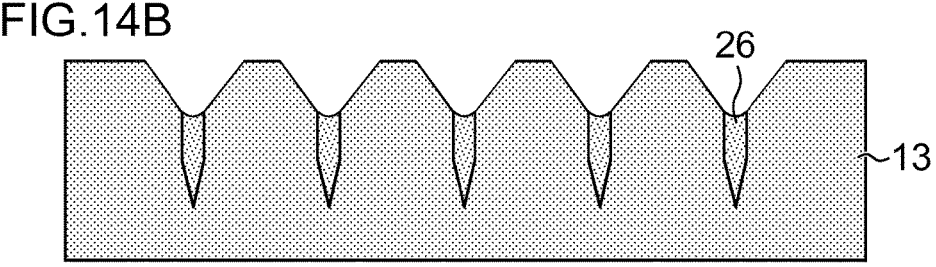
FIG. 14B is a diagram illustrating the another process of forming the polymer sheet.
Figure 14C:
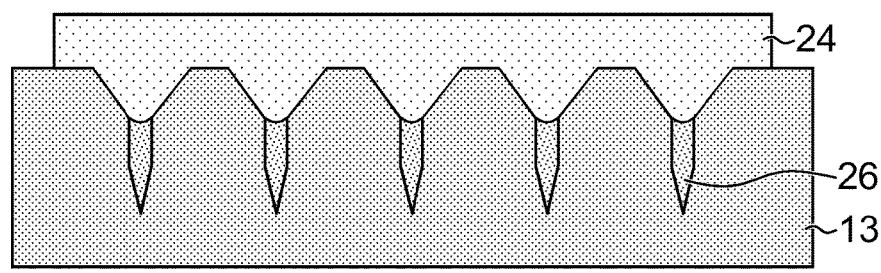
FIG. 14C is a diagram illustrating the another process of forming the polymer sheet.

Now, a second embodiment is described with reference to FIGS. 14A to 14D. As depicted in FIG. 14A, the needle-like recessed portions 15 in the mold 13 are filled with the drug-containing solution 22 through the nozzle 34. Then, as depicted in FIG. 14B, the drug-containing solution 22 is dried and solidified to form the drug-containing layer 26 in each of the needle-like recessed portions 15. When the drug-containing solution 22 is dried and solidified, the tip of the needle-like recessed portion 15 can be filled with the drug-containing solution 22 by the pressurization from the front surface of the mold 13 and the reduced pressure suction from the back surface of the mold 13. Then, as depicted in FIG. 14C, the non-drug-containing solution 24 is applied onto the surface of the drug-containing layer 26 using the dispenser. In addition to the coating using the dispenser, for example, a bar coating method, a spin coating method, and an application using a spray or the like are applicable. Since the drug-containing layer 26 is solidified, the drug in the drug-containing layer 26 can be restrained from diffusing to the non-drug-containing solution 24.

Figure 14D:
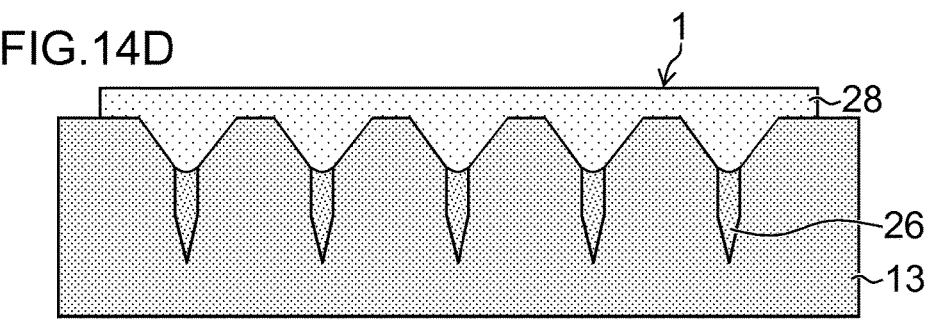
FIG. 14D is a diagram illustrating the another process of forming the polymer sheet.

Then, as depicted in FIG. 14D, the non-drug-containing solution 24 is dried and solidified to form the polymer sheet 1 including the drug-containing layer 26 and the non-drug-containing layer 28.

In the second embodiment, pressurization from the front surface of the mold 13 and reduced pressure suction from the back surface of the mold 13 are preferably performed in order to promote filling of the inside of the needle-like recessed portions 15 with the drug-containing solution 22 and the non-drug-containing solution 24.

Figure 15A:
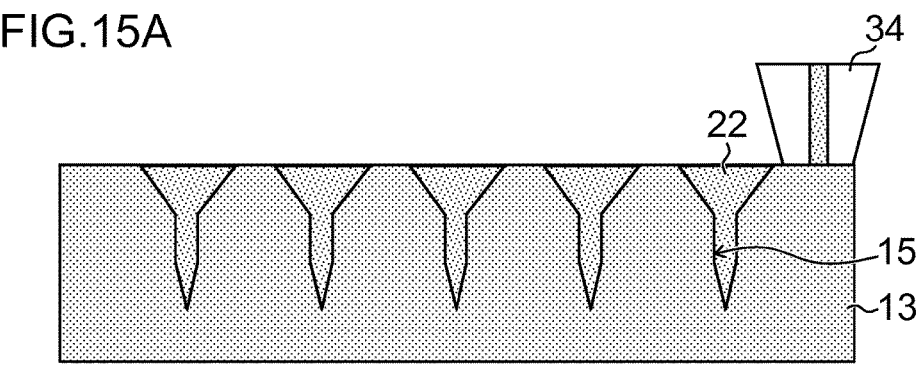
FIG. 15A is a diagram illustrating yet another process of forming the polymer sheet.
Figure 15B:
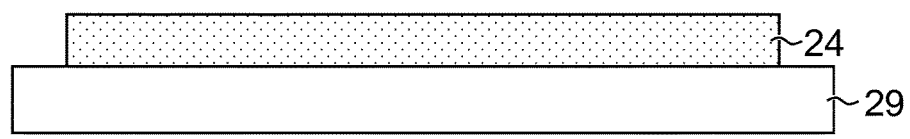
FIG. 15B is a diagram illustrating the yet another process of forming the polymer sheet.
Figure 15C:
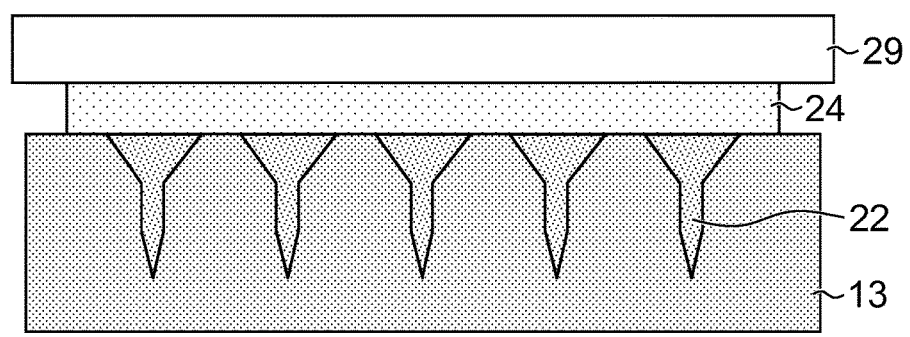
FIG. 15C is a diagram illustrating the yet another process of forming the polymer sheet.
Figure 15D:
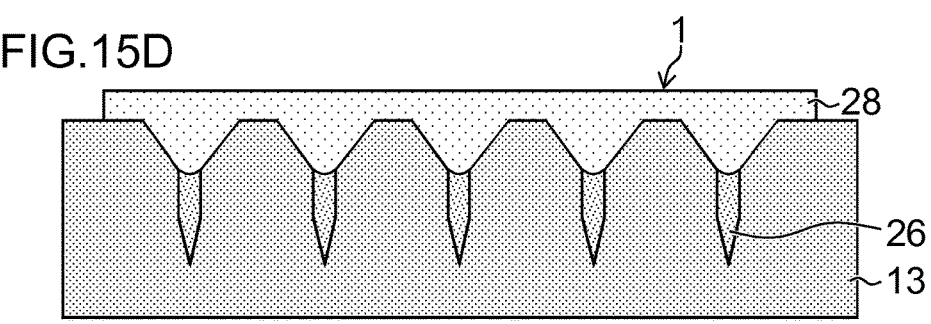
FIG. 15D is a diagram illustrating the yet another process of forming the polymer sheet.

Now, a third embodiment is described with reference to FIGS. 15A to 15D. As depicted in FIG. 15A, the needle-like recessed portions 15 in the mold 13 are filled with the drug-containing solution 22 through the nozzle 34. Then, as depicted in FIG. 15B, the non-drug-containing solution 24 is applied onto a surface of another support 29. The support 29 is not limited, but for example, polyethylene, polyethylene terephtalate, polycarbonate, polypropylene, an acrylic resin, triacetylcellulose, or glass may be used. Then, as depicted in FIG. 15C, the non-drug-containing solution 24 formed on the support 29 is laid on the mold 13 with the needle-like recessed portions 15 filled with the drug-containing solution 22. Then, as depicted in FIG. 15D, the drug-containing solution 22 and the non-drug-containing solution 24 are dried and solidified to form the polymer sheet 1 including the drug-containing layer 26 and the non-drug-containing layer 28.

In the third embodiment, pressurization from the front surface of the mold 13 and reduced pressure suction from the back surface of the mold 13 are preferably performed in order to promote filling of the inside of the needle-like recessed portions 15 with the drug-containing solution 22.

In formation of the polymer sheet 1, the step of drying and solidification is a step in which the drug-containing solution 22 and/or the non-drug-containing solution 24 is dried to solidify the drug-containing solution 22 and/or the non-drug-containing solution 24 in each of the needle-like recessed portions 15.

A method for drying the drug-containing solution 22 and/or the non-drug-containing solution 24 may be a step of volatilizing a solvent in the polymer solution. The method is not particularly limited, and for example, a method such as heating, air blowing, or pressure reduction may be used. Specifically, a method of blowing warm air against the solution at 0.1 to 10 m/s may be used.

The warm air is preferably at a temperature at which the drug in the drug-containing solution 22 is not thermally degraded. The drug-containing solution 22 is solidified by means of drying and contracted compared to the state of the drug-containing solution 22 at the time of application. Thus, the drug-containing layer 26 can be easily peeled off from the needle-like recessed portions 15 in the mold 13.

The non-drug-containing solution 24 similarly contracts, and thus, the contraction occurs in the direction of film thickness of the sheet given that the solidified drug-containing layer 26 and/or non-drug-containing layer 28 is in tight contact with the mold 13, reducing the film thickness. Furthermore, when the drug-containing layer 26 and/or non-drug-containing layer 28 peels off from the mold 13 during drying, the polymer sheet 1 also contracts in a surface direction and is thus distorted or curled. When the polymer sheet 1 is peeled off from the mold 13 in the state in which the drug-containing layer 26 and/or non-drug-containing layer 28 in the needle-like recessed portions 15 is not sufficiently dried, a defect is likely to occur in which the shapes of the needle-like protruding portions on the polymer sheet 1 are broken or bent. Thus, the polymer sheet 1 is preferably not peeled off from the mold 13 during drying.

After the polymer sheet 1 with the needle-like protruding portions each formed on a surface of the sheet 1 and including the drug-containing layer 26 composed of the drug-containing solution 22 and the non-drug-containing layer 28 composed of the non-drug-containing solution 24 is formed, the process proceeds to a peeling-off step of peeling the polymer sheet 1 off from the mold 13.

Figure 16:
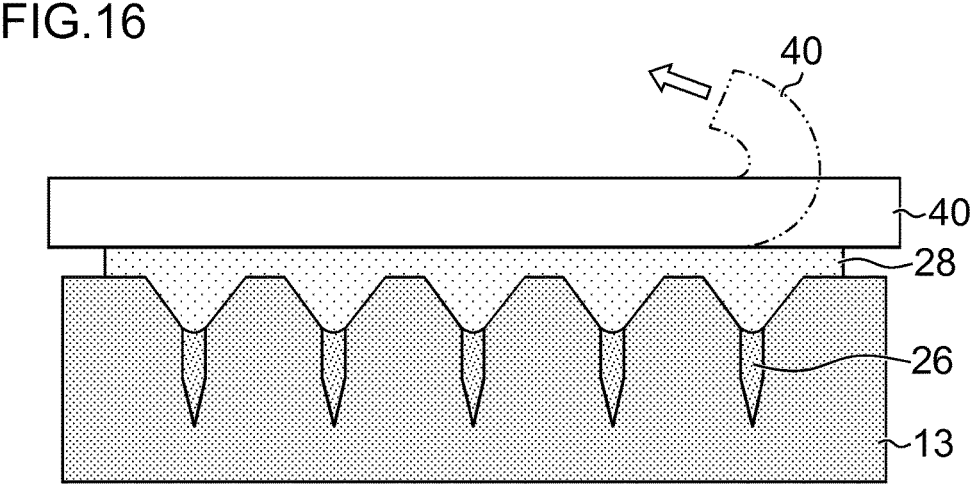
FIG. 16 is a diagram illustrating a peeling-off step.
Figure 17:
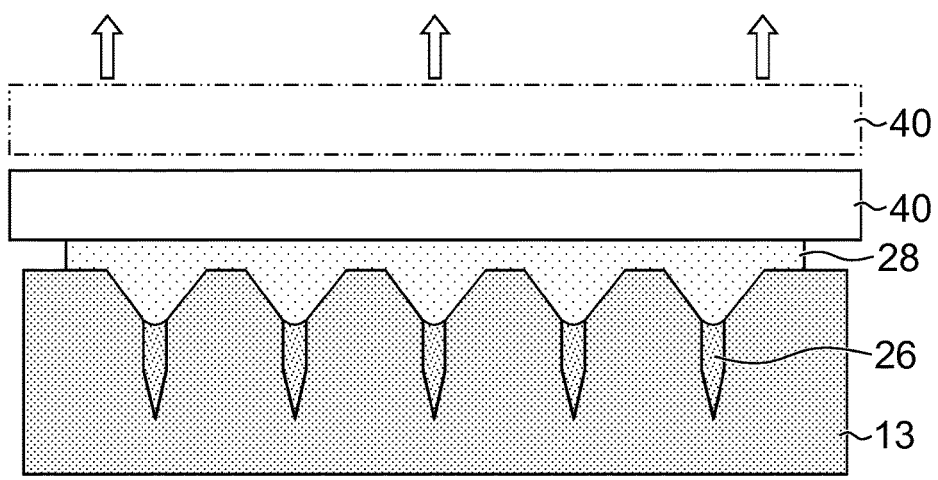
FIG. 17 is a diagram illustrating another peeling-off step.

A method for peeling the polymer sheet 1 off from the mold 13 is not limited. The needle-like protruding portions are desirably prevented from being bent or broken at the time of peeling-off. Specifically, as depicted in FIG. 16, a sheet-like base material 40 provided with a sticky adhesive layer is attached onto the polymer sheet 1, and then the polymer sheet 1 can be peeled off by turning the base material 40 over at an end of the polymer sheet 1. However, this method may cause the needle-like protruding portions to be bent. Thus, as depicted in FIG. 17, a method may be applied in which suckers (not depicted in the drawings) are installed on the base material 40 on the polymer sheet 1 and the base material 40 is then sucked using air and lifted perpendicularly. The support 29 may also be used as the base material 40.

Normally, when a structure with needle-like protruding portions with a high aspect ratio is peeled off from the mold 13 as in the present embodiment, high stress is applied due to a large contact area. The needle-like protruding portions that are microneedles may be destroyed and remain in the needle-like recessed portions 15 instead of being peeled off from the mold 13, and a transdermal-absorption sheet produced may be defective. Thus, in the present embodiment, the mold 13 is preferably composed of a material that is very easy to peel off. Furthermore, the mold 13 composed of a highly elastic soft material allows relaxation of stress applied to the microneedles at the time of peeling-off.

Figure 18:
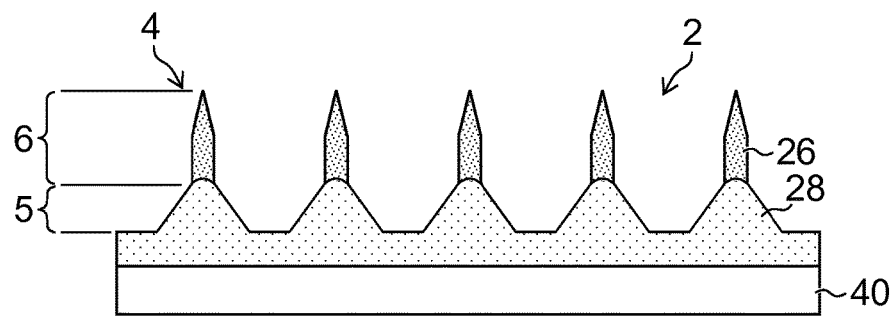
FIG. 18 is a diagram illustrating still yet another process of forming the polymer sheet.

FIG. 18 depicts a transdermal-absorption sheet 2 composed of the polymer sheet 1 peeled off from the mold 13. The transdermal-absorption sheet 2 is composed of the base material 40, the drug-containing layer 26 formed on the base material 40, and the layer 28 not substantially containing the drug. Needle-like protruding portions 4 on the transdermal-absorption sheet 2 are each composed of a truncated cone portion 5 and a needle portion 6 on the truncated cone portion 5. The needle portion 6 mainly has a conical or pyramidal needle portion and a cylindrical or rectangular columnar body portion. However, the needle-like protruding portions 4 are not limited to this shape.

EXAMPLES

The present invention is further specifically described using examples of the present invention. Materials, usages, rates, the contents of processing, the processing procedures and the like illustrated in the following examples may be changed as needed unless the change departs from the spirits of the present invention. Thus, the scope of the present invention should not be interpreted in a limited manner based on the specific examples illustrated below.

Example 1

(Production of the Mold)

Figure 19:
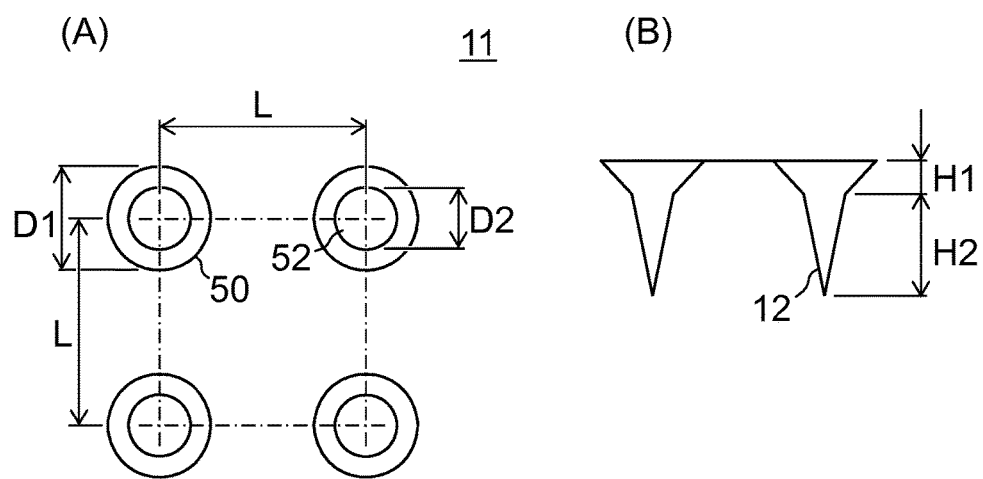
FIG. 19 is a plan view and a side view of an original plate.

FIG. 19 depicts an original plate for the mold. Portion (A) of FIG. 19 is a plan view, and portion (B) of FIG. 19 is a side view. The original plate 11 as depicted in FIG. 19 was produced by grinding a surface of a smooth Ni plate having a side of 40 mm so as to form shape portions 12 each with a needle-like structure that are arranged at a pitch L of 1,000 μm in two-dimensional array with 10 columns and 10 rows. Each shape portions 12 with a needle-like structure includes: a truncated cone 50 with a bottom surface diameter D1 of 500 μm and a height H1 of 150 μm; and a cone 52 formed on the truncated cone 50 and having a diameter D2 of 300 μm and a height H2 of 500 μm. A film was formed on the original plate 11 to have a thickness of 0.6 mm using silicone rubber (SILASTIC (registered trademark), MDX4-4210 (product number) manufactured by Dow Corning Toray Co., Ltd.). The film was thermally cured with tips of the cones of the original plate 11 allowed to protrude 50 μm from a surface of the film and was then peeled off. Thus, an inverted article made of silicone rubber was produced which had through-holes with a diameter of approximately 30 μm. The inverted article made of silicone rubber was trimmed so as to leave a planar portion with a side of 30 mm on whose central portion needle-like recessed portions were formed with two-dimensionally arranged in 10 columns and 10 rows. The portion thus obtained was used as a mold. A surface of the mold corresponding to the wider opening of each of the needle-like protruding portions was the front surface of the mold. A surface of the mold with the through-holes (air vent holes) with a diameter of 30 μm was the back surface of the mold.

(Preparation of the Drug-Containing Solution)

Hydroxyethyl starch (manufactured by Fresenius Kabi) was dissolved into water to prepare an 8% water solution. As a drug, 2 wt % human serum albumin (manufactured by Wako Pure Chemical Industries, Ltd.) and 0.7 mass % Evans blue dye (manufactured by Wako Pure Chemical Industries, Ltd.) were added to the solution to obtain the drug-containing solution.

(Formation of the Drug-Containing Layer)

A gas permeable film (NTF-8031 (product number) manufactured by NITTO DENKO CORPORATION) with a side of 15 mm was placed on a horizontal vacuum platform, and the mold was installed on the gas permeable film with the front surface of the mold facing upward. The back surface of the mold was decompressed with a suction pressure of 50 kPa to fix the gas permeable film and the mold to the vacuum platform. A SUS (stainless steel) nozzle shaped as depicted in FIG. 8 was prepared, and a slit-like opening with a length of 12 mm and a width of 0.2 mm was formed in the center of a lip portion with a length of 20 mm and a width of 2 mm. The nozzle was attached to a syringe. The inside of the syringe and the nozzle was filled with the drug-containing solution of 3 mL. The nozzle was aligned in order for the opening to be parallel to the first line composed of a plurality of needle-like recessed portions formed in the front surface of the mold. The nozzle was pressed against the mold with a pressure of 0.14 kgf/cm$^2$ at a distance of 2 mm from the first line in a direction opposite to the second line. While the nozzle, kept pressed against the mold, was moved in a direction perpendicular to the length direction of the opening at 1 mm/sec, the drug-containing solution was discharged using the dispenser through the opening at 0.31 μL/sec for 10 seconds. Movement of the nozzle was stopped at a distance of 2 mm from the tenth line of the plurality of two-dimensionally arranged needle-like recessed portions in a direction opposite to the ninth line. The nozzle was then separated from the mold.

The mold filled with the drug-containing solution as described above was cut at a position around and 1 mm outside the plurality of two-dimensionally arranged needle-like recessed portions. Drying was performed in a thermohygrostat bath at 30° C. and 40% for 30 minutes to form the drug-containing layer. After the drying, a tape with a low adhesive force was attached to the front surface of the mold and then peeled off to remove the drug-containing layer adhering to areas other than the needle-like recessed portions in the mold.

(Measurement of the Content of the Drug)

The mold and the tape with the low adhesive force were each immersed in 1 mL of water in a 5 mL lidded container. The lid of the container was loosened, and the mold and the tape were pressurized in a pressurized-type degassing unit at 0.5 MPa for 10 minutes. The container was then closed, and ultrasonic cleaning was carried out for 30 minutes. After it was confirmed that no dye remained on the mold and the tape with the low adhesive force, each of the solutions was measured for absorbance at a wavelength of 620 nm using a microplate absorbance reader (Sunrise Series manufactured by TECAN). The contents of the drug-containing layer in the needle-like recessed portions and in the areas other than the needle-like recessed portions in the mold were calculated.

Example 2

(Production of the Mold)

Using the original plate produced in Example 1, silicone rubber was formed into a film having a thickness of 0.7 mm, thermally cured without through-holes being formed in the back surface thereof, and peeled off to produce the inverted article of the silicone rubber.

(Preparation of the Drug-Containing Solution)

The drug-containing solution was prepared as is the case with Example 1.

(Formation of the Drug-Containing Layer)

The mold was installed on the horizontal vacuum platform with the front surface of the mold facing upward. The back surface of the mold was decompressed with a suction pressure of 50 kPa to fix the mold to the vacuum platform. A SUS (stainless steel) nozzle shaped as depicted in FIG. 8 was prepared, and a slit-like opening with a length of 12 mm and a width of 0.2 mm was formed in the center of the lip portion with a length of 20 mm and a width of 2 mm. The nozzle was attached to the syringe. The inside of the syringe and the nozzle was filled with the drug-containing solution of 3 mL. The nozzle was aligned in order for the opening to be parallel to the first line composed of the plurality of needle-like recessed portions formed in the front surface of the mold. The nozzle was pressed against the mold with a pressure of 0.42 kgf/cm$^2$ at a distance of 2 mm from the first line in the direction opposite to the second line.

The nozzle, kept pressed against the mold, was moved in the direction perpendicular to the length direction of the opening at 1 mm/sec. The nozzle was stopped when the opening in the nozzle reached the central position of the first line of needle-like recessed portions. The nozzle was pushed into the mold with a pressure of 2.8 kgf/cm$^2$. Moreover, air was blown through the inside of the nozzle to pressure the mold at 0.2 MPa ($\approx$2.0 kgf/cm$^2$) for one minute. Thus, the needle-like recessed portions in the first line in the mold were filled with the drug-containing solution.

The pressure in the nozzle was released, and then the pressing pressure of the nozzle against the mold was recovered to 0.42 kgf/cm$^2$. The nozzle, kept pressed against the mold, was moved to the central position of the needle-like recessed portions in the second line. Movement of the nozzle was stopped, and the needle-like recessed portions in the second line in the mold were filled with the drug-containing solution as is the case with the first line. This was repeated to fill up to the tenth line of needle-like recessed portions with the drug-containing solution. Movement of the nozzle was stopped at a distance of 2 mm from the tenth line of the plurality of two-dimensionally arranged needle-like recessed portions. The nozzle was then separated from the mold.

The mold filled with the drug-containing solution as described above was cut at a position around and 1 mm outside the plurality of two-dimensionally arranged needle-like recessed portions. The mold was dried in the thermohygrostat bath at 30° C. and 40% for 30 minutes to form the drug-containing layer. After the drying, a tape with a low adhesive force was attached to the front surface of the mold and then peeled off to remove the drug-containing layer adhering to the areas other than the needle-like recessed portions in the mold.

The mold and the tape with the low adhesive force were each immersed in 1 mL of water in a 5 mL lidded container. The lid of the container was loosened, and the mold and the tape were pressurized in the pressurized-type degassing unit at 0.5 MPa for 10 minutes. The container was then closed, and ultrasonic cleaning was carried out for 30 minutes. After it was confirmed that no dye remained on the mold and the tape with the low adhesive force, each of the solutions was measured for absorbance at a wavelength of 620 nm using a microplate absorbance reader (Sunrise Series manufactured by TECAN). The contents of the drug-containing layer in the needle-like recessed portions and in the areas other than the needle-like recessed portions in the mold were calculated. The content of the drug-containing layer was calculated as is the case with Example 1.

Example 3

The contents of the drug-containing layer in the needle-like recessed portions and in the areas other than the needle-like recessed portions in the mold were calculated as is the case with Example 2 except that, in formation of the drug-containing layer, the pressing pressure on the nozzle and the mold was changed from 0.42 kgf/cm$^2$ to 0.83 kgf/cm$^2$.

(Evaluation 1)

Table 1 depicts evaluation results for Examples 1 to 3.

TABLE 1

| | Mold | Pressing pressure [kgf/cm2] | Filling amount of drug-containing layer in needle-like recessed portions [mg] | Deposition amount of drug-containing layer in areas other than needle-like recessed portions [mg] |
|---|---|---|---|---|
| Example 1 | Through-holes formed in back surface | 0.14 | 0.287 | 0.0003 |
| Example 2 | No through-hole in back surface | 0.42 | 0.216 | — |
| Example 3 | No through-hole in back surface | 0.83 | 0.187 | — |

With respect to the volume of the inside of the needle-like recessed portions in the mold was 3.10 µL (equivalent to 0.310 mg in terms of a density of 1), the needle-like recessed portions were filled with the appropriate amount of drug-containing layer in all of Examples 1 to 3. The amount of drug adhering to the areas other than the needle-like recessed portions increases as pressing pressure decreases. In the examples, even in Example 1 with the lowest pressing pressure, the amount of drug adhering to the areas other than the needle-like recessed portions was approximately 0.1% of the amount of drug in the needle-like recessed portions.

Example 4

(Production of the Mold)

The mold was produced as is the case with Example 2.

(Preparation of the Drug-Containing Solution)

Hydroxyethyl starch (manufactured by Fresenius Kabi) was dissolved into water to prepare an 8% water solution. As a drug, a mixed solution of 0.25 mass % human growth hormone (growth hormone, human, recombinant, for biochemistry; manufactured by Wako Pure Chemical Industries, Ltd.) and 0.001 mass % FITC (manufactured by PD Research, FACS-Dl (product number)) was added to the water solution to obtain the drug-containing solution.

(Preparation of the Non-Drug-Containing Solution)

Chondroitin sulfate (manufactured by Maruha Nichiro Corporation) was dissolved into water to prepare a 30% water solution as a non-drug-containing solution.

(Formation of the Drug-Containing Layer)

The drug-containing layer was formed as is the case with Example 1.

(Formation of the Non-Drug-Containing Layer)

The non-drug-containing solution was applied onto a surface of slide glass with a film thickness of 210 µm. The mold was placed on the slide glass such that the front surface of the mold was brought into contact with the applied film and pneumatically pressed in the pressurized-type degassing unit (TAC Series manufactured by SAKURA SEIKI Co., Ltd.) at 0.35 MPa for 10 minutes. The slide glass was taken out of the pressurized-type degassing unit, and placed in the thermohygrostat bath (small environmental test chamber manufactured by ESPEC) with the slide glass facing downward to be dried at 30° C. and 40% for eight hours. The slide glass corresponds to the support 29 and the base material 40 described above.

(Peeling-Off Step)

The mold, along with the gas permeable film, was peeled off from the polymer layer on the slide glass. On the slide glass, a transdermal-absorption sheet with a three-dimensional array structure was formed which was composed of the drug-containing layer and the non-drug-containing layer and in which the human growth hormone was eccentrically located in the tip.

The transdermal-absorption sheet produced as described above was evaluated for a drug filling rate to the needle-like protruding portions. As an evaluation method, the transdermal-absorption sheet was observed using a confocal fluorescence microscope (manufactured by NIKON CORPORATION; C1plus+TE2000U (product number)). The rate of the FITC (fluorescein isothiocyanate) fluorescence intensity of a 350-µm portion of the tip of each needle-like protruding portion in the FITC fluorescence intensity of the whole transdermal-absorption sheet was measured as the filling rate. Then, the filling rate was approximately 75%, indicating that the tip of the needle portion was filled with the drug at a high rate.

Example 5

(Production of the Mold)

The mold was produced as is the case with Example 2.

(Preparation of the Drug-Containing Solution)

The drug-containing solution was prepared as is the case with Example 4.

(Preparation of the Non-Drug-Containing Solution)

Hydroxyethyl starch (manufactured by Fresenius Kabi) and sodium hyaluronate (molecular weight: 900 thousand to 1.5 million; manufactured by Maruha Nichiro Corporation) were dissolved into water in the ratio of 39:1 to prepare a 40% water solution as a non-drug-containing solution.

(Formation of the Drug-Containing Layer)

The drug-containing layer was formed as is the case with Example 1.

(Formation of the Non-Drug-Containing Layer)

The non-drug-containing layer was formed as is the case with Example 4.

(Peeling-Off Step)

The peeling-off step was executed as is the case with Example 4.

The transdermal-absorption sheet produced as described above was evaluated for the drug filling rate to the needle-like protruding portions. In the evaluation method, the transdermal-absorption sheet was observed using the confocal fluorescence microscope (manufactured by NIKON CORPORATION; C1plus+TE2000U). The rate of the FITC fluorescence intensity of a 350-µm portion of the tip of each needle-like protruding portion in the FITC fluorescence intensity of the whole transdermal-absorption sheet was measured as the filling rate. Then, the filling rate was approximately 65%, indicating that the tip of the needle portion was filled with the drug at a high rate.

Example 6

(Production of the Mold)

The mold was produced as is the case with Example 1.

(Preparation of the Drug-Containing Solution)

The drug-containing solution was prepared as is the case with Example 4.

(Preparation of the Non-drug-Containing Solution)

The non-drug-containing solution was prepared as is the case with Example 4.

(Formation of the Drug-Containing Layer)

The drug-containing layer was formed as is the case with Example 1.

(Formation of the Non-Drug-Containing Layer)

The non-drug-containing solution was applied onto the surface of the slide glass with a film thickness of 210 µm. The slide glass was placed on the drug-containing layer formed on the mold which was placed on the vacuum platform via the gas permeable film so that the applied surface was brought into contact with the drug-containing layer, and was further decompressed at a suction pressure of 50 kPa for 20 minutes.

The decompression was turned off, and the structure in which the layers from the gas permeable film to the slide glass were in tight contact with one another was removed from the vacuum platform. The sample was placed in the thermohygrostat bath (small environmental test chamber manufactured by ESPEC) with the slide glass facing downward to be dried at 30° C. and 40% for eight hours.

(Peeling-Off Step)

The peeling-off step was performed as is the case with Example 4.

The transdermal-absorption sheet produced as described above was evaluated for the filling rate to the needle-like protruding portions. In the evaluation method, the transdermal-absorption sheet was observed using the confocal fluorescence microscope (manufactured by NIKON CORPORATION; C1plus+TE2000U). The rate of the FITC fluorescence intensity of a 350-µm portion of the tip of each needle-like protruding portion in the FITC fluorescence intensity of the whole transdermal-absorption sheet was measured as the filling rate. Then, the filling rate was approximately 75%, indicating that the tip of the needle portion was filled with the drug at a high rate.

Example 7

(Production of the Mold)

The mold was produced as is the case with Example 1.

(Preparation of the Drug-Containing Solution)

The drug-containing solution was prepared as is the case with Example 4.

(Preparation of the Non-Drug-Containing Solution)

Hydroxyethyl starch (manufactured by Fresenius Kabi) and sodium hyaluronate (molecular weight: 900 thousand to 1.5 million; manufactured by Maruha Nichiro Corporation) were dissolved into water in the ratio of 39:1 to prepare a 40% water solution as a non-drug-containing solution. Moreover, chondroitin sulfate (manufactured by Maruha Nichiro Corporation) was dissolved into water to prepare a 10% water solution as an intermediate layer solution.

(Formation of the Drug-Containing Layer)

The drug-containing layer was formed as is the case with Example 1.

(Formation of the Non-Drug-Containing Layer)

The non-drug-containing solution was applied onto the surface of the slide glass with a film thickness of 200 µm, and the slide glass was then dried in the thermohygrostat bath at a temperature of 60° C. and a relative humidity of 20% for one hour. The slide glass was then taken out of the thermohygrostat bath. The intermediate layer solution was applied to the surface of the applied film after the drying with a film thickness of 100 µm. The slide glass was then placed on the drug-containing layer formed on the mold placed on the vacuum platform via the gas permeable film so that the applied surface of the intermediate layer solution was brought into contact with the drug-containing layer, and was further decompressed at a suction pressure of 50 kPa for 20 minutes.

The decompression was turned off, and the sample was removed from the vacuum platform in a state where the layers from the gas permeable film to the slide glass were brought into tight contact with each other. The sample was placed in the thermohygrostat bath (small environmental test chamber manufactured by ESPEC) with the slide glass facing downward to be dried at 30° C. and 40% for eight hours.

(Peeling-Off Step)

The peeling-off step was performed as is the case with Example 4.

The transdermal-absorption sheet produced as described above was evaluated for the drug filling rate to the needle-like protruding portions. In the evaluation method, the transdermal-absorption sheet was observed using the confocal fluorescence microscope (manufactured by NIKON CORPORATION; C1plus+TE2000U). The rate of the FITC fluorescence intensity of a 350-µm portion of the tip of each needle-like protruding portion in the FITC fluorescence intensity of the whole transdermal-absorption sheet was measured as the filling rate. Then, the filling rate was approximately 65%, indicating that the tip of the needle portion was filled with the drug at a high rate.

What is claimed is:

1. A method for manufacturing a transdermal-absorption polymer sheet with needle-like protruding portions including a drug-containing layer and a non-drug-containing layer, the method comprising:
    a step of providing a mold with needle-like recessed portions that are arranged in a two-dimensional array and a liquid feeding apparatus comprising a nozzle with a lip surface and a slit-shaped opening formed on the lip surface;
    a step of filling the two-dimensionally arranged needle-like recessed portions with a drug-containing solution by repeating a filling step of feeding the drug-containing solution from the liquid feeding apparatus to the mold and filling one or more of the needle-like recessed portions constituting one line of the two-dimensional array with the drug-containing solution through the nozzle aligned over the needle-like recessed portions in a state where the nozzle and a front surface of the mold are brought in contact with each other, and a moving step of moving the liquid feeding apparatus relative to the mold in a direction perpendicular to a longitudinal direction of the opening in a state where the nozzle and the front surface of the mold are brought in contact with each other;
    a step of forming a polymer sheet provided with needle-like protruding portions having an inverted shape of the needle-like recessed portions on the surface of the polymer sheet, the needle-like protruding portions each comprising a drug-containing layer composed of the drug-containing solution and a non-drug-containing layer composed of a non-drug-containing solution; and
    a step of peeling the polymer sheet off from the mold,
    wherein the step of forming the polymer sheet includes:
        solidifying the drug-containing solution so as to form the drug-containing layer of the needle-like protruding portions,
        providing a non-drug-containing solution to the mold after the solidification step, and
        solidifying the non-drug-containing solution so as to form the non-drug-containing layer of the needle-like protruding portions,
    wherein the non-drug-containing solution is a polymer solution, and
    wherein, in the moving step, feeding of the drug-containing solution from the liquid feeding apparatus to the mold is started before the nozzle is positioned over a first line of the needle-like recessed portions in the direction of the relative movement between the nozzle and the mold, and the feeding of the drug-containing solution to the mold is stopped before the nozzle is positioned over a last line of the needle-like recessed portions in the direction of the relative movement between the nozzle and the mold.

2. The method for manufacturing the transdermal-absorption polymer sheet according to claim 1, wherein, in the filling step, the two-dimensionally arranged needle-like recessed portions are filled with the drug-containing solution so that filling is performed on one line or a plurality of lines at a time.

3. The method for manufacturing the transdermal-absorption polymer sheet according to claim 1, wherein the filling step comprises pressurizing an inside of the nozzle.

4. The method for manufacturing the transdermal-absorption polymer sheet according to claim 3, wherein, in the filling step, a pressing force with which the nozzle and the mold are brought into contact with each other is equal to or stronger than a pressurizing force inside the nozzle.

5. The method for manufacturing the transdermal-absorption polymer sheet according to claim 1, wherein the filling step comprises sucking a back surface of the mold with a reduced pressure.

6. The method for manufacturing the transdermal-absorption polymer sheet according to claim 4, wherein the pressing force with which the nozzle and the mold are brought into contact with each other in the filling step is stronger than a pressing force with which the nozzle and the mold are brought into contact with each other in the moving step.

7. The method for manufacturing the transdermal-absorption polymer sheet according to claim 1, wherein, in the moving step, feeding of the drug-containing solution from the liquid feeding apparatus to the mold is stopped while the nozzle is positioned over an area other than the needle-like recessed portions in the mold.

8. The method for manufacturing the transdermal-absorption polymer sheet according to claim 1, wherein at least one of the nozzle and the front surface of the mold is made of an elastically deformable raw material.

9. The method for manufacturing the transdermal-absorption polymer sheet according to claim 1, wherein the mold comprises an air vent hole at a tip of each of the needle-like recessed portions.

10. The method for manufacturing the transdermal-absorption polymer sheet according to claim 1, wherein the step of forming the polymer sheet comprises a step of feeding the non-drug-containing solution to the mold with the needle-like recessed portions filled with the drug-containing solution, and then drying and solidifying the drug-containing solution and the non-drug-containing solution to form the drug-containing layer and the non-drug-containing layer.

11. The method for manufacturing the transdermal-absorption polymer sheet according to claim 1, wherein the step of forming the polymer sheet comprises a step of drying and solidifying the drug-containing solution filled in the needle-like recessed portions in the mold to form the drug-containing layer, feeding the non-drug-containing solution to the mold in which the drug-containing layer is formed in the needle-like recessed portions, and then drying and solidifying the non-drug-containing solution to form the non-drug-containing layer.

12. The method for manufacturing the transdermal-absorption polymer sheet according to claim 1, wherein the step of forming the polymer sheet comprises a step of applying the non-drug-containing solution onto a surface of another support, attaching the another support onto which the non-drug-containing solution is applied to the mold with the needle-like recessed portions filled with the drug-containing solution, and drying and solidifying the drug-containing solution and the non-drug-containing solution to form the drug-containing layer and the non-drug-containing layer.

13. The method for manufacturing the transdermal-absorption polymer sheet according to claim 10, wherein the step of forming the polymer sheet comprises performing at least one of pressurization from the front surface of the mold and reduced pressure suction from the back surface of the mold, when drying and solidifying the drug-containing solution contained in the needle-like recessed portions in the mold.

14. The method for manufacturing the transdermal-absorption polymer sheet according to claim 10, wherein the step of forming the polymer sheet comprises performing at least one of pressurization of the non-drug-containing solution from a front surface of the mold and reduced pressure suction of the non-drug-containing solution from a back surface of the mold.

15. The method for manufacturing the transdermal-absorption polymer sheet according to claim 1, wherein a drug is peptide, protein, nucleic acid, polysaccharide, a vaccine, a medical compound belonging to a water-soluble low-molecular-weight compound, or a cosmetic component.

16. The method for manufacturing the transdermal-absorption polymer sheet according to claim 1, wherein the needle-like protruding portions comprise the drug-containing layer and the non-drug-containing layer, the drug-containing layer further contains hydroxyethyl starch, and the non-drug-containing layer contains hydroxyethyl starch and hyaluronic acid.

17. The method for manufacturing the transdermal-absorption polymer sheet according to claim 1, wherein the needle-like protruding portions comprise the drug-containing layer and the non-drug-containing layer, the drug-containing layer further contains chondroitin sulfate, and the non-drug-containing layer contains hydroxyethyl starch.

18. The method for manufacturing the transdermal-absorption polymer sheet according to claim 1, wherein a width of the slit-shaped opening on the lip surface in the direction of the relative movement is smaller than a width of the needle-like recessed portions in the direction of the relative movement, and a width of a contact portion of the nozzle and the front surface of the mold is larger than the width of the needle-like recessed portions in the direction of the relative movement.

19. The method for manufacturing the transdermal-absorption polymer sheet according to claim 1, wherein a width of a contact portion of the nozzle and the front surface of the mold in a longitudinal direction is the same with a width of two-dimensionally arranged needle-like recessed portions in the longitudinal direction.

\* \* \* \* \*